US012397076B2

United States Patent
Leibowitz

(10) Patent No.: US 12,397,076 B2
(45) Date of Patent: Aug. 26, 2025

(54) METHOD AND APPARATUS FOR SANITIZATION OF HAND COVERINGS

(71) Applicant: Ian Leibowitz, Sugar Land, TX (US)

(72) Inventor: Ian Leibowitz, Sugar Land, TX (US)

(*) Notice: Subject to any disclaimer, the term of this patent is extended or adjusted under 35 U.S.C. 154(b) by 150 days.

(21) Appl. No.: 17/917,444

(22) PCT Filed: Sep. 2, 2021

(86) PCT No.: PCT/US2021/048916
§ 371 (c)(1),
(2) Date: Oct. 6, 2022

(87) PCT Pub. No.: WO2022/060579
PCT Pub. Date: Mar. 24, 2022

(65) Prior Publication Data
US 2023/0149574 A1 May 18, 2023

Related U.S. Application Data

(60) Provisional application No. 62/706,903, filed on Sep. 16, 2020.

(51) Int. Cl.
*A61L 2/10* (2006.01)
*A61L 2/28* (2006.01)
*A61B 42/60* (2016.01)

(52) U.S. Cl.
CPC ............ *A61L 2/28* (2013.01); *A61L 2/10* (2013.01); *A61B 42/60* (2016.02); *A61L 2202/11* (2013.01); *A61L 2202/14* (2013.01); *A61L 2202/26* (2013.01)

(58) Field of Classification Search
None
See application file for complete search history.

(56) References Cited

U.S. PATENT DOCUMENTS

| 4,785,478 | A | 11/1988 | Mosley |
| 4,993,199 | A | 2/1991 | Hughes |
| 5,827,431 | A | 10/1998 | Jones |
| 5,947,275 | A | 9/1999 | Hess |
| 6,254,625 | B1 | 7/2001 | Rosenthal |

(Continued)

FOREIGN PATENT DOCUMENTS

| CA | 2807337 | 8/2014 |
| CN | 104170577 | 12/2014 |

(Continued)

OTHER PUBLICATIONS

Rachel Green, Can You Reuse Disposable Gloves?, Online Article, 43154, Nexon Hygiene (website), Nettleham, Lincolnshire, England, N/A, https://www.nexonhygiene.co.uk/blog/2018/02/can-you-reuse-disposable-gloves/.

(Continued)

*Primary Examiner* — Regina M Yoo
(74) *Attorney, Agent, or Firm* — Adair Myers Stevenson Yagi PLLC; Matthew Compton

(57) ABSTRACT

A hand sanitization system, a sanitization machine, and hand coverings containing markings for use with the sanitization machine are disclosed. The hand sanitization machine is capable of sanitizing hand coverings that were traditionally disposed of after one use. The hand coverings may contain indicators that signal when they have been sterilized.

11 Claims, 25 Drawing Sheets

(56) References Cited

U.S. PATENT DOCUMENTS

| | | |
|---|---|---|
| 6,343,425 B1 | 2/2002 | Sias et al. |
| 6,495,100 B1 | 12/2002 | Lin et al. |
| 6,656,424 B1 | 12/2003 | Deal |
| 6,662,807 B2 | 12/2003 | Meinschewnk |
| 7,020,624 B2 | 3/2006 | Hsuan |
| 7,323,065 B2 | 1/2008 | Fencl et al. |
| 8,021,608 B2 | 9/2011 | Brown-Skrobot et al. |
| 8,077,555 B1 | 12/2011 | Lovato |
| 8,083,998 B2 | 12/2011 | Hurwitz et al. |
| 8,142,713 B2 | 3/2012 | Gordon |
| 8,318,090 B2 | 11/2012 | Gordon |
| 8,399,854 B1 | 3/2013 | Crawford |
| 8,400,310 B2 | 3/2013 | Brow |
| 8,564,424 B2 | 10/2013 | Evarts et al. |
| 8,578,548 B1 | 11/2013 | Costello |
| 8,633,816 B2 | 1/2014 | Snodgrass et al. |
| 8,799,011 B2 | 8/2014 | Wilson et al. |
| 8,813,302 B1 | 8/2014 | Capito |
| 8,844,766 B2 | 9/2014 | Zaima et al. |
| 8,854,337 B2 | 10/2014 | Nakanishi |
| 8,941,588 B2 | 1/2015 | Minnen |
| 8,941,590 B2 | 1/2015 | Csaszar et al. |
| 8,992,324 B2 | 3/2015 | Guild et al. |
| 8,992,837 B2 | 3/2015 | Jung et al. |
| 9,011,607 B2 | 4/2015 | De Luca et al. |
| 9,044,521 B2 | 6/2015 | Farren |
| 9,104,271 B1 | 8/2015 | Adams |
| 9,179,703 B2 | 11/2015 | Shur et al. |
| 9,308,558 B2 | 4/2016 | Ackermann et al. |
| 9,311,809 B2 | 4/2016 | Diaz |
| 9,387,268 B2 | 7/2016 | Farren |
| 9,418,535 B1 | 8/2016 | Felch et al. |
| 9,486,021 B2 | 11/2016 | Keil et al. |
| 9,572,903 B2 | 2/2017 | Dobrinsky et al. |
| 9,592,313 B2 | 3/2017 | Stull, Jr. et al. |
| 9,603,960 B2 | 3/2017 | Dobrinsky et al. |
| 9,662,411 B2 | 5/2017 | Rizzone |
| 9,687,575 B2 | 6/2017 | Farren |
| 9,707,306 B2 | 7/2017 | Farren |
| 9,713,757 B2 | 7/2017 | Wiseman et al. |
| 9,881,485 B2 | 1/2018 | Hajdenberg |
| 9,891,718 B2 | 2/2018 | Connor |
| 9,965,943 B2 | 5/2018 | Borke et al. |
| 10,010,634 B2 | 7/2018 | Bonutti et al. |
| 10,016,575 B2 | 7/2018 | Vazales et al. |
| 10,046,073 B2 | 8/2018 | Farren et al. |
| 10,102,735 B2 | 10/2018 | Easter |
| 10,121,356 B2 | 11/2018 | Wallace et al. |
| 10,146,323 B1 | 12/2018 | Keyes et al. |
| 10,166,686 B1 | 1/2019 | Dhanjal et al. |
| 10,183,085 B2 | 1/2019 | Dobrinsky et al. |
| 10,195,300 B2 | 2/2019 | Lloyd |
| 10,235,412 B2 | 3/2019 | Underkoffler et al. |
| 10,248,200 B2 | 4/2019 | Cohen et al. |
| 10,255,466 B2 | 4/2019 | Jinadatha |
| 10,265,540 B2 | 4/2019 | Yehezkel |
| 10,275,025 B2 | 4/2019 | Black et al. |
| 10,279,058 B2 | 5/2019 | Lin et al. |
| 10,286,094 B2 | 5/2019 | Dobrinsky et al. |
| 10,362,989 B2 | 7/2019 | McMillen et al. |
| 10,363,330 B2 | 7/2019 | Bettles et al. |
| 10,376,605 B1 | 8/2019 | Majdali et al. |
| 10,438,476 B2 | 10/2019 | Sengstaken, Jr. |
| 10,445,747 B2 | 10/2019 | Farioli Brioschi et al. |
| 10,456,487 B2 | 10/2019 | Bilenko et al. |
| 10,548,687 B2 | 2/2020 | Benning |
| 10,556,027 B2 | 2/2020 | Kreiner et al. |
| 10,596,288 B2 | 3/2020 | Bettles et al. |
| 10,603,394 B2 | 3/2020 | Farren et al. |
| 10,639,387 B2 | 5/2020 | Bonutti et al. |
| 10,646,602 B2 * | 5/2020 | Jung ............... G06Q 10/087 |
| 10,687,598 B2 | 6/2020 | Lakios et al. |
| 10,751,434 B2 | 8/2020 | Bonutti et al. |
| 10,751,435 B2 | 8/2020 | Wyman |
| 10,751,495 B2 | 8/2020 | Klee et al. |
| 10,814,025 B2 | 10/2020 | Bonutti et al. |
| 10,818,157 B1 | 10/2020 | Koester et al. |
| 10,835,704 B1 | 11/2020 | Heimbuch et al. |
| 10,850,184 B1 | 12/2020 | Colvin et al. |
| 2003/0021723 A1 | 1/2003 | Lopez Ordaz |
| 2003/0197122 A1 | 10/2003 | Faiola |
| 2004/0028553 A1 | 2/2004 | Panico |
| 2005/0093485 A1 | 5/2005 | Spivak |
| 2006/0059603 A1 | 3/2006 | Peng |
| 2006/0147339 A1 | 7/2006 | Hunter |
| 2006/0188389 A1 | 8/2006 | Levy |
| 2006/0216193 A1 | 9/2006 | Johnson |
| 2007/0192986 A1 | 8/2007 | Garcia |
| 2007/0222554 A1 | 9/2007 | Hart |
| 2008/0199354 A1 | 8/2008 | Gordon |
| 2008/0216208 A1 | 9/2008 | Sanders |
| 2009/0195385 A1 | 8/2009 | Huang |
| 2009/0199857 A1 | 8/2009 | Peake et al. |
| 2009/0205664 A1 | 8/2009 | Lyon |
| 2009/0224907 A1 | 9/2009 | Sinha |
| 2009/0276239 A1 | 11/2009 | Swart et al. |
| 2009/0314308 A1 | 12/2009 | Kim |
| 2010/0266446 A1 | 10/2010 | Constantacos |
| 2011/0025509 A1 | 2/2011 | Brow |
| 2011/0044848 A1 | 2/2011 | Wright |
| 2012/0256742 A1 | 10/2012 | Snodgrass |
| 2013/0048876 A1 | 2/2013 | Crawford |
| 2013/0263895 A1 | 10/2013 | Lee |
| 2013/0268293 A1 | 10/2013 | Knudson |
| 2013/0323119 A1 | 12/2013 | Alwan |
| 2014/0070950 A1 | 3/2014 | Snodgrass |
| 2014/0301893 A1 | 10/2014 | Stroup et al. |
| 2014/0327545 A1 | 11/2014 | Bolling |
| 2015/0037201 A1 | 2/2015 | Armour et al. |
| 2015/0151012 A1 * | 6/2015 | Ritz ............... A61N 5/0616 250/492.1 |
| 2015/0209457 A1 | 7/2015 | Bonutti et al. |
| 2015/0289728 A1 | 10/2015 | Penaz |
| 2015/0297767 A1 | 10/2015 | Gaska et al. |
| 2016/0030766 A1 | 2/2016 | Scritchfiel et al. |
| 2016/0158395 A1 | 6/2016 | Sweeney |
| 2016/0175066 A1 | 6/2016 | Swinney |
| 2016/0354503 A1 | 12/2016 | Hutchens et al. |
| 2017/0080117 A1 * | 3/2017 | Gordon ............... A61L 2/084 |
| 2018/0218591 A1 | 8/2018 | Easter |
| 2018/0221520 A1 | 8/2018 | Nguyen |
| 2018/0276681 A1 | 9/2018 | Farioli Brioschi et al. |
| 2018/0357886 A1 | 12/2018 | Tavori |
| 2019/0043337 A1 | 2/2019 | Liu et al. |
| 2019/0051138 A1 | 2/2019 | Easter |
| 2019/0107887 A1 | 4/2019 | Bazor et al. |
| 2019/0172336 A1 | 6/2019 | Haidegger et al. |
| 2020/0101183 A1 | 4/2020 | Dijkstra et al. |
| 2020/0229884 A1 | 7/2020 | Djie |
| 2020/0237941 A1 * | 7/2020 | Bonutti ............... C02F 1/36 |
| 2020/0261608 A1 | 8/2020 | Crosby et al. |
| 2020/0285341 A1 | 9/2020 | De Araujo et al. |
| 2020/0297879 A1 | 9/2020 | Bonutti et al. |
| 2020/0297880 A1 | 9/2020 | Bonutti et al. |
| 2020/0306396 A1 | 10/2020 | Bonutti et al. |
| 2020/0309703 A1 | 10/2020 | Luk |
| 2020/0320793 A1 | 10/2020 | Marcolina et al. |
| 2020/0323603 A1 | 10/2020 | Bayly et al. |
| 2020/0375276 A1 | 12/2020 | Insley |
| 2020/0384139 A1 | 12/2020 | Ahn et al. |
| 2020/0384140 A1 | 12/2020 | Hoehne |
| 2020/0390915 A1 | 12/2020 | David et al. |
| 2020/0390918 A1 | 12/2020 | Eidman |
| 2021/0170192 A1 * | 6/2021 | Wang ............... A61N 5/0616 |
| 2021/0177999 A1 * | 6/2021 | Ogihara ............... A61L 2/10 |
| 2021/0353807 A1 * | 11/2021 | Ogihara ............... A61L 2/10 |
| 2022/0001044 A1 | 1/2022 | Burd |
| 2022/0040343 A1 | 2/2022 | Stillman |

FOREIGN PATENT DOCUMENTS

| | | |
|---|---|---|
| CN | 106858840 | 6/2017 |
| CN | 208286452 | 12/2018 |
| CN | 210009127 | 2/2020 |

(56) References Cited

FOREIGN PATENT DOCUMENTS

| | | |
|---|---|---|
| CN | 210204908 | 3/2020 |
| CN | 111529071 | 8/2020 |
| CN | 111544121 | 8/2020 |
| CN | 211156234 | 8/2020 |
| EP | 1973578 | 10/2008 |
| JP | 2020062392 | 4/2020 |
| TW | 200302113 | 8/2003 |
| WO | 1996014765 | 5/1996 |
| WO | 2002102421 | 12/2002 |
| WO | 2009065128 | 5/2009 |
| WO | 2015116833 | 8/2015 |
| WO | 2016012488 | 1/2016 |
| WO | 2016069701 | 5/2016 |
| WO | 2019084203 | 5/2019 |
| WO | 2020007398 | 1/2020 |
| WO | 2020249161 | 12/2020 |
| WO | WO 2021/195008 | 9/2021 |

OTHER PUBLICATIONS

Safe Work Australia, FIFI & DIDO > Gloves, Website, 43950, Safe Work Australia, Australia, N/A, https://covid19.swa.gov.au/covid-19-information-workplaces/industry-information/fifo-dido/gloves.

Anna Gragert, How to Clean and Disinfect Rubber Gloves, Online Article, 43942, Leaf Group LTD./ Leaf Group Lifestyle, Santa Monica, California, USA, N/A, https://www.hunker.com/13421162/how-to-sanitize-rubber-gloves.

Anna Gragert, How to Wash Latex Gloves, Online Article, 43945, Leaf Group LTD./ Leaf Group Lifestyle, Santa Monica, California, USA, N/A, https://www.hunker.com/13422209/how-to-wash-latex-gloves.

OSHA, Hand Hygiene and Protective Gloves in Hurricane Affected Areas, Online Fact Sheet, Sep. 2005, US Department of Labor, USA, N/A, https://www.osha.gov/OshDoc/data_Hurricane_Facts/hand_hygiene_and_gloves.pdf.

Monica Torres, Can You Wash and Reuse Disposable Gloves?, Online Article, 43929, HuffPost Home & Living/Verizon Media, USA, N/A, https://www.huffpost.com/entry/disposable-gloves-washed-reused_I_5e8df7a7c5b61ada15c121ab.

Templeton, Michael, Basic Principles of UV Disinfection , Powerpoint Slides, , Department of Civil and Environmental Engineering, Imperial College London, London, England, N/A, https://www.un-ihe.org/sites/default/files/3_-_templeton.pdf.

United States Food & Drug Administration, Questions About Personal Protective Equipment (PPE), Website, 43901, US Food & Drug Administration, USA, N/A, https://www.fda.gov/medical-devices/personal-protective-equipment-infection-control/questions-about-personal-protective-equipment-ppe.

Paige Pfleger, Technology to Clean and Reuse PPE is Being Deployed to Hotspot Hospitals, Online Article, 43920, National Public Radio (NPR), USA, N/A, https://www.npr.org/2020/03/30/823803831/technology-to-clean-and-reuse-ppe-is-being-deployed-to-hotspot-hospitals.

Clean Hands Safe Hands, Patients (webpage), Website, , Clean Hands—Safe Hands LLC, USA, N/A, https://cleanhands-safehands.com/patients/.

Tom J. Blodgett, Reminder Systems to Reduce Duration of Indwelling Urinary Catheters: A Narrative Review, Online Article, 40386, US National Library of Medicine National Institutes of Health, USA, Urol Nurs. Sep.-Oct. 2009; 29(5) 369-379, https://www.ncbi.nlm.nih.gov/pmc/articles/PMC2910409/.

Hughes Environmental, UVC Light Disinfection, Website, , Hughes Environmental, USA, N/A, https://hughesenv.com/uvc-light-disinfection/.

Gazdik, Edward et al. , "Determination of the Attenuation Properties of Laboratory Gloves Exposed to an Ultraviolet Transilluminator.", Journal Article, 40407, Journal of Occupational and Environmental Hygiene , USA, vol. 1:6. pp. 391-402, doi: 10.1080/15459620490452013.

Heßling, Martin et al. , "Ultraviolet irradiation doses for coronavirus inactivation—review and analysis of coronavirus photoinactivation studies.", Journal Article, 43965, GMS hygiene and infection control , Germany, vol. 15 Doc08, doi:10.3205/dgkh000343.

Malayeri, Adel Haji et al. , "Fluence (UV Dose) Required to Achieve Incremental Log Inactivation of Bacteria, Protozoa, Viruses and Algae.", Online Article, Fall 2016, IUVA News , Chevy Chase, MD, USA, vol. 18:3. , https://uvsolutionsmag.com/stories/pdf/archives/180301_UVSensitivityReview_full.pdf.

American Conference of Governmental Industrial Hygienists, Ultraviolet Radiation: TLV® Physical Agents 7th Edition Documentation. , Online Article, , University of Ottawa, Ottowa, Canada, N/A, https://orm.uottawa.ca/my-safety/em-radiation/uv/exposure-limits.

\* cited by examiner

METHOD AND APPARATUS FOR SANITIZATION OF HAND COVERINGS

RELATED APPLICATIONS

This patent application is a national stage filing under 35 U.S.C. § 371 of PCT Application No. PCT/US2021/048916 filed Sep. 2, 2021 and entitled "METHOD AND APPARATUS FOR SANITIZATION OF HAND COVERINGS" which PCT application claims the benefit of U.S. Provisional Patent Application No. 62/706,903 filed Sep. 16, 2020, and the disclosure of each of the foregoing is incorporated by reference herein in their entirety.

FIELD OF THE INVENTION

The present invention generally relates to the sanitization of gloves or other hand coverings.

BACKGROUND OF THE INVENTION

In jobs that include high manual interaction with the public including but not limited to cashiers, service personnel at post offices, receptionists, retail sales, food or beverage servers, and so forth, the current state-of-the-art to protect against pathogen transmission is to cover hands with disposable gloves. Gloves are not changed between customers or cleaned in any way. Changing gloves between customers is generally impractical and time consuming.

Not only are service personnel unlikely to change gloves between customers, but in even slightly humid or hot locales, changing gloves often is inconvenient, cumbersome, and can be difficult as the hands become sweaty and the gloves become difficult to put on due to the increased friction caused by damp, sweaty, and in some cases swollen hands. It also may be cost prohibitive to change gloves between customers and gloves are often in short supply or suffer from distribution issues. This results in an environment that allows for the spread of pathogens between customers as gloves become contaminated after interacting with, and exchanging objects with, customers.

Gloves as currently used in this and other environments, where the server personnel do not change gloves between customers, are less effective or do not aid in decreasing the spread of pathogens due to the high degree of cross contamination that occurs between customers, from objects and items passed between service personnel and a customer, and the service personnel touching surfaces while serving the customer.

Additionally, in jobs that require a high level of cleanliness including but not limited to jobs in biological laboratories, healthcare settings, and food processing facilities, workers are supposed to change and dispose of gloves after handling potentially contaminated items. Workers often only remove and dispose of gloves after their shift or before a break. Workers touch various objects during their shift, with potentially contaminated gloves. Surfaces that have been touched by contaminated gloves can therefore become a reservoir for pathogens. If a worker touches the contaminated surface, they can contaminate more surfaces and potentially allow pathogens to contaminate other objects that leave a facility. Pathogens in such facilities can be especially dangerous because in such facilities pathogens are often exposed to substances designed to kill them, meaning that the pathogens that survive are resistant to different things used against them such as antibiotics, cleaning chemicals, vaccines, etc. Even more problematically, workers in such facilities also have been proven to not change and dispose of gloves as often as health regulations require.

Prior art sterilizing machines use ultra-violet light to sterilize various things. Limiting ultraviolet exposure to the body may be important when considering a device that is designed to be used after every interaction with a customer, which may total to be in the hundreds if not thousands for a single service person in just a single shift. If not properly protected, the hands may quickly be exposed to a dangerous dose of ultraviolet light. The prior art fails to account for the many potential safety issues that come with exposing gloved hands to ultraviolet light.

Also, a device to treat the surface of gloves is most effective when it is used consistently and often. Many workers fail to comply with simple health protocols such as washing hands after using the restroom, so it is important to use various methods to ensure that workers comply with any new biosecurity protocols.

Since contamination of the surface of gloves is highly variable as it is not limited to just biological contamination but also physical or chemical contamination, often it is not only important to ensure that the gloves are treated after different interactions, but also to ensure that after some types of contaminations the gloves are changed.

SUMMARY OF THE INVENTION

The present invention relates to a system that allows hand coverings such as gloves or other types of hand coverings to be reused quickly while eliminating, deactivating, or disabling all or a significant amount of surface pathogens, thereby decreasing transmission of pathogens by touch. The system may result in lower costs and is often more practical than changing gloves after every customer which is time consuming, unwieldy and may not be possible due to limited resources. Use of embodiments of the present invention is often typically easier and faster than merely changing gloves, as the touched surfaces of a pair of hand coverings can be sanitized in seconds between customers.

The specialized hand coverings used in some embodiments allow for safe sterilization of the coverings with minimal, if any, exposure of skin or eyes to the ultraviolet light from the disinfecting apparatus, which in some cases may be a prior art sterilizing machine with a UV light source, or an embodiment of one of the present inventions herein. To be able to maintain safe operation of an ultraviolet treatment of gloved hands, the system can verify certain safety factors before emitting ultraviolet light. A distinguishing visual feature may be used in conjunction with optical sensors on the sterilization machine to safely activate the germicidal light source. Alternatively, optimal placement of the hand coverings within the device, so as to prevent over insertion of the covered hand beyond a point, can be indicated by a mark on the sleeve of the hand covering and/or detected by a sensor and/or limited by a mechanical barrier. The hand coverings also ensure that the highest contact surfaces of the covering may be disinfected between each customer.

Additionally, the hand coverings and/or the machine and/or a device attached to a service person may indicate to customers that the hand coverings have been cleaned recently by auditory, visual, tactile, and/or other signals, providing the customer and service personnel with reassurance and confidence thus enhancing bio-security and perhaps equally important to the customer, the feeling of security. The indicating device may have an indicator in the form of a visual, audible, tactile, and/or other signal indicating that the service person's gloves have been exposed to the device.

In one embodiment, the indicating device may indicate that treatment had occurred within the time set or may also be set to be triggered by an input from a point-of-sale system, or a "next served" number counting system, or a proximity sensor sensing the absence of a customer at a counter or place of service, or the triggering of a sensor by the presence of new customer. All of which may be implemented individually or collectively to trigger a visual, audible, tactile, and/or other signal indicating that the gloved hands need to be reinserted into the device to re-expose the surfaces to the disinfecting light. Once reinserted and treated for the set time given the light source and type, the timer (which may be integrated into the controller), light indicator, other visual, tactile, audible, and/or other signals will be reset for another interval of time and/or service of the next customer in the queue.

DETAILED DESCRIPTION

The present invention is described with reference to the attached figures. The figures are not drawn to scale. Several aspects of embodiments of the invention are described below. It should be understood that numerous specific details, relationships, and methods are set forth to provide an understanding of the invention. One skilled in the relevant art, however, will readily recognize that the invention can be practiced without one or more of the specific details or with other methods.

FIGS. 1-6 are depictions of various embodiments of a sterilizing machine. Though the embodiments in FIGS. 1-6 are shown in a rectangular shape, the machine can be created in many shapes and sizes which may include, but are not limited to, a rectangular prism, sphere, hexagonal prism, pyramid, oval, cylindrical, or some other generally regular or otherwise irregular shape.

Figure 1:
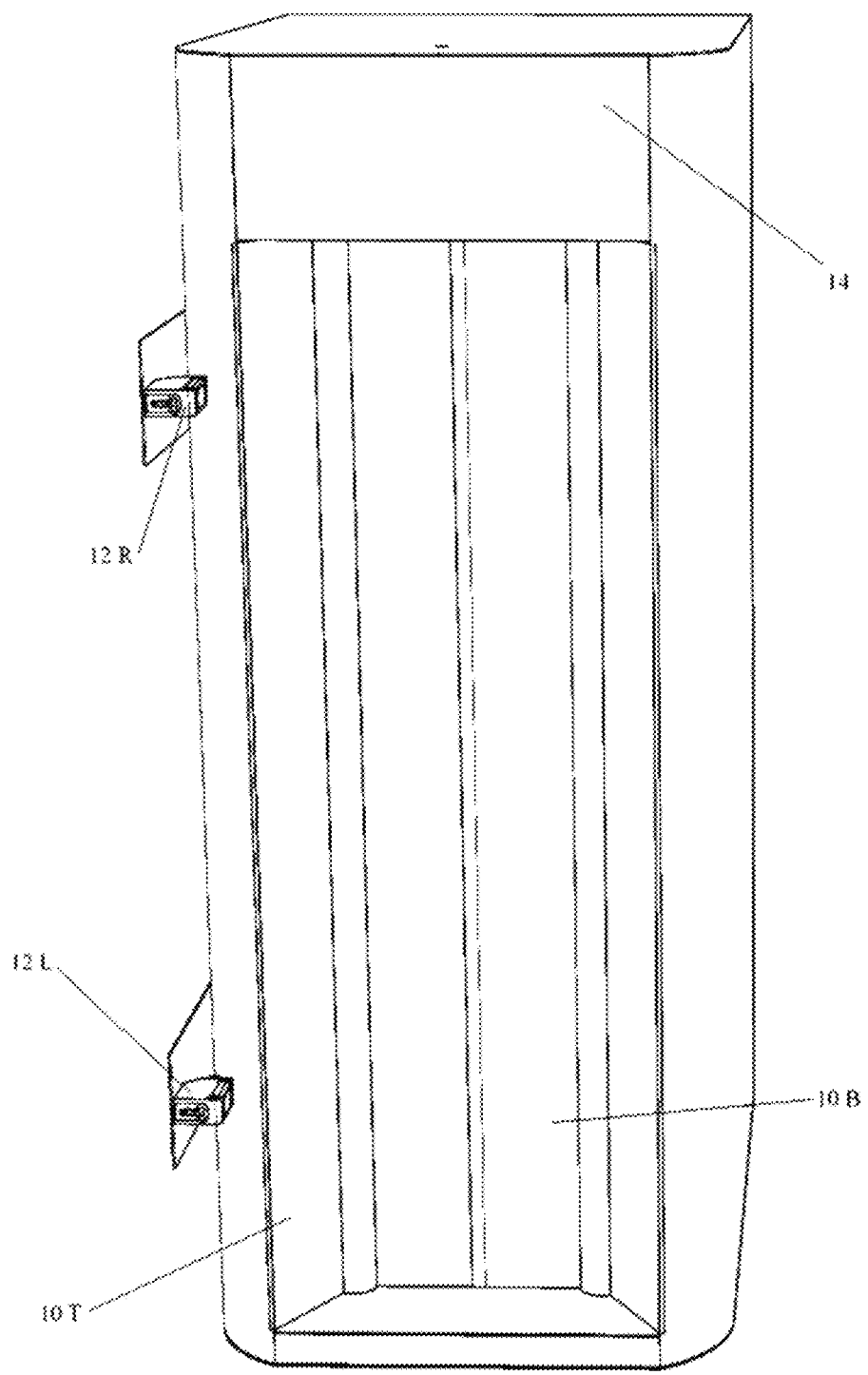
FIG. 1 depicts a front view of an embodiment showing a sterilizing machine portion of a system for rapid sanitization of hand coverings.

In FIG. 1, the sterilizing machine is constructed from a rectangular prism body assembly 14. The two brushes 10B and 10T act as a baffling that reduces the light amount and intensity of light that exits the body assembly 14 in order to protect the user. The body assembly 14 also has mounted thereto two photoelectric sensors 12L and 12R.

Figure 2:
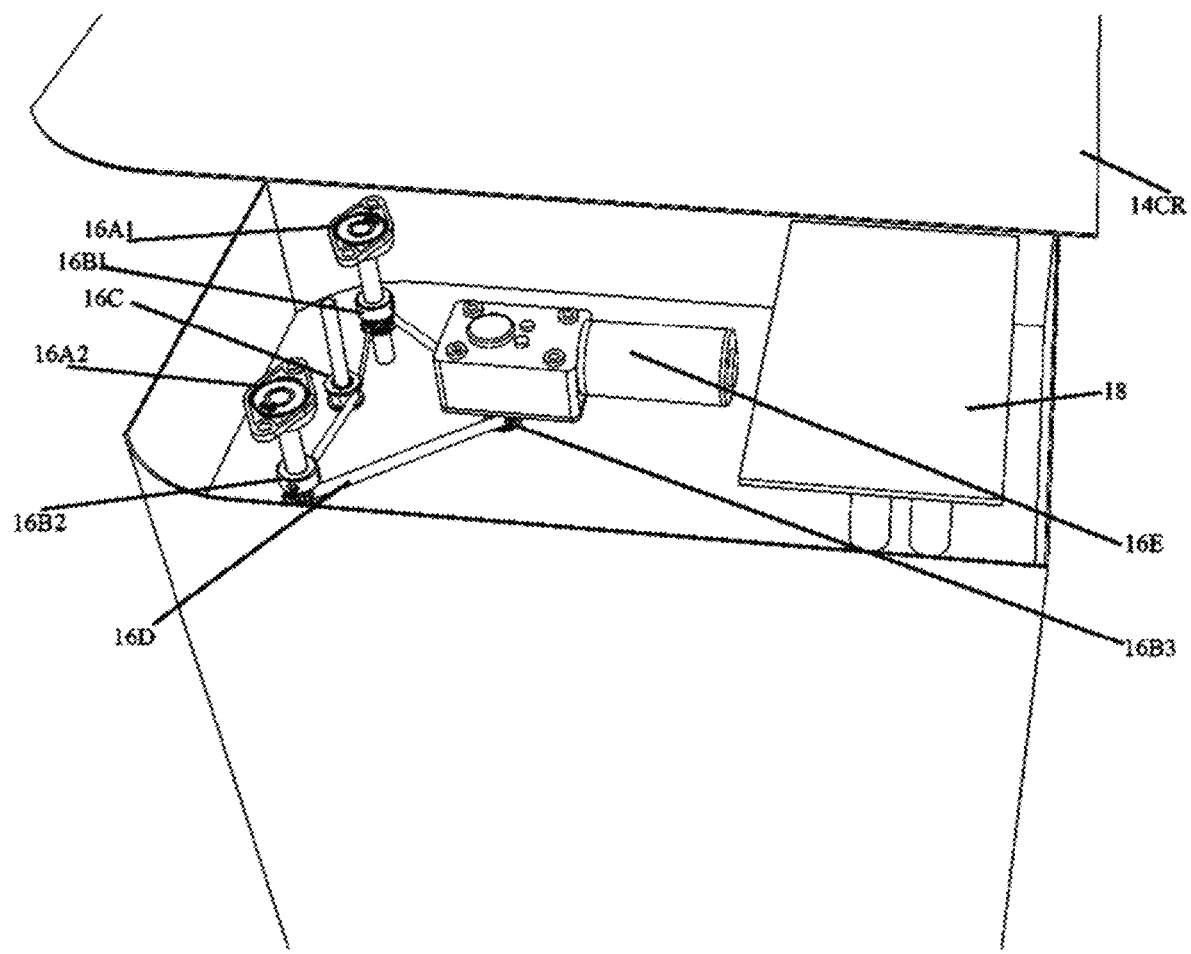
FIG. 2 depicts another embodiment of a sterilizing machine showing a brush drive mechanism and controller for the sterilizing machine portion of a system.
Figure 3:
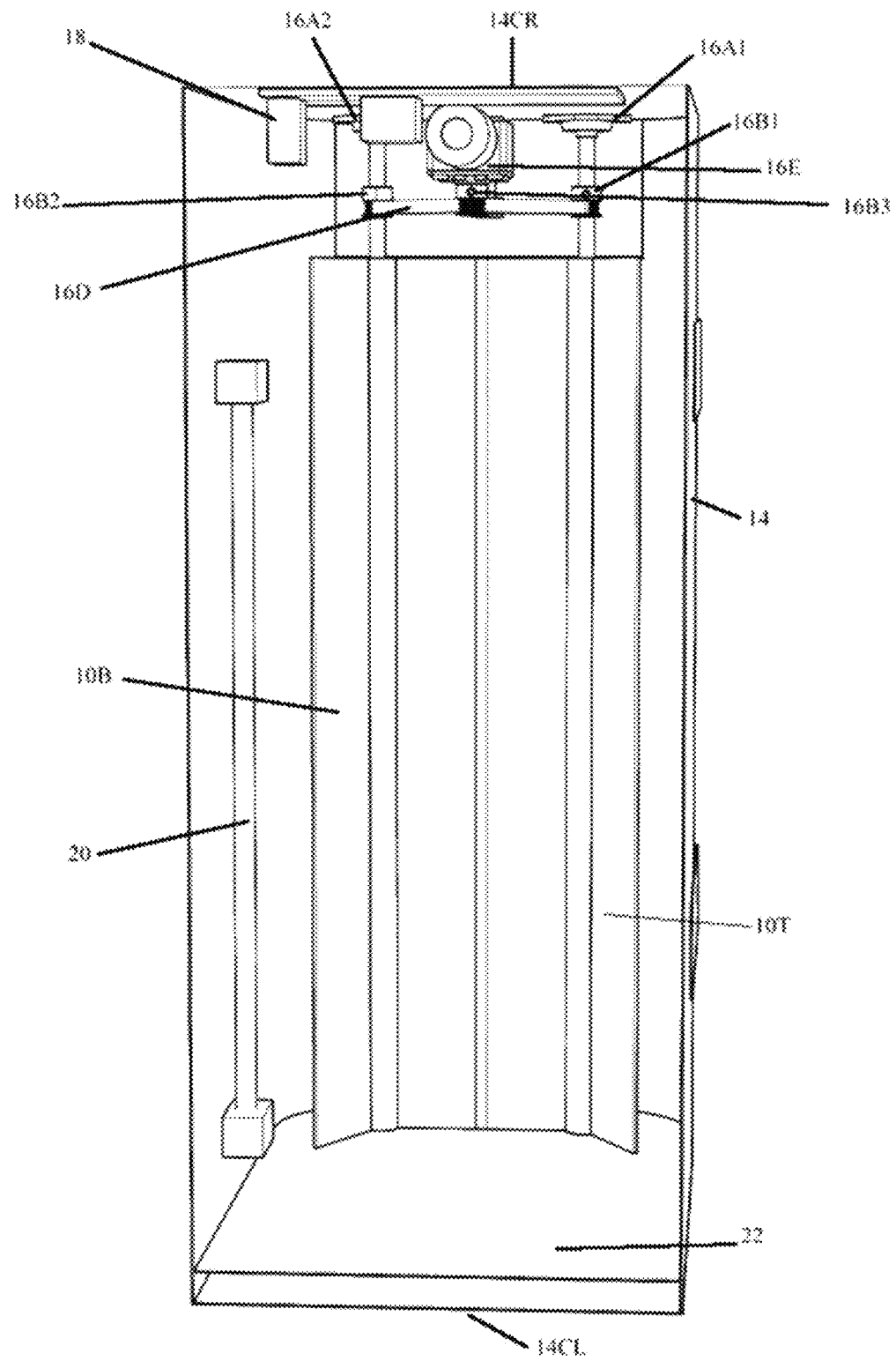
FIG. 3 depicts another embodiment of a sterilizing machine with the back panel removed, showing a flash tube, reflective interior panels, brushes, brush drive and controller.

In FIG. 2, bearings 16A1 and 16A2 are mounted to the cover 14CR at a distance to allow for the two brushes 10B and 10T (shown in FIG. 1) to effectively block all, or effectively all, of the light of the xenon flash tube assembly 20 (shown in FIG. 3). Also affixed to the brushes 10B and 10T on the right side, inside of the right cover 14CR, are pulleys 16B1 and 16B2 with one pulley on each brush on the right side of the machine. The belt 16D will run on these pulleys with an idler tensioner 16C between the bearings 16A1 and 16A2 used to hold the brushes 10B and 10T in place. The idler tensioner 16C is mounted on the right cover 14CR in a way to allow it to tension the belt 16D. The belt runs to the motor and gearbox 16E that may also be mounted to the right cover 14CR. The motor and gearbox 16E has a pulley 16B3 installed on its shaft, where the belt will run. The UV light controller 18 may also be mounted to the cover 14CR.

In FIG. 3, on the left side of the machine there are bearings 16A1 and 16A2 (not shown) mounted to the left cover 14CL. The body assembly 14 has a xenon flash tube assembly 20 mounted to its bottom. The xenon flash tube assembly 20 is connected using wires to the UV light controller 18. The controller 18 is mounted to the cover 14CR. In addition, the drive assembly 16 is mounted to the cover 14CR. Bearings 16A1 and 16A2 are mounted to the cover 14CR at a distance to allow for the two brushes 10B and 10T to effectively block all, or effectively all, of the light of the xenon flash tube assembly 20. The bearings 16A1 and 16A2 allow the brushes 10B and 10T to be inserted and fastened in translational stillness while allowing rotational freedom driven by belt 16D in conjunction with pulleys 16B1 and 16B2 and 16B3 and motor and gearbox 16E. The two brushes 10B and 10T act as a baffling that reduces the light amount and intensity of light that exits the body assembly 14 in order to protect the user. Left interior cover plate 22L is attached to body assembly 14.

Figure 25A:
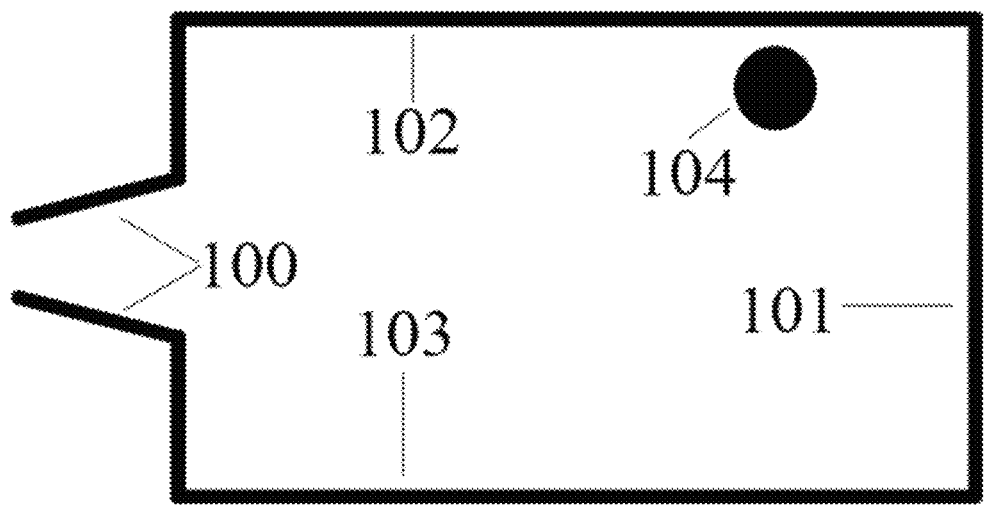
FIG. 25A depicts a cross section of a sterilizing machine depicting an alternative baffle design.
Figure 25B:
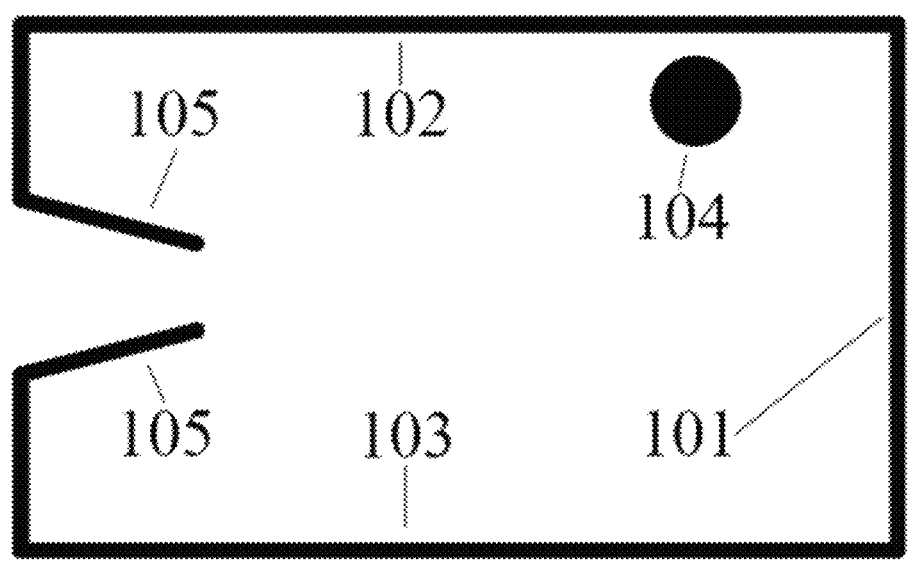
FIG. 25B depicts a cross section of a sterilizing machine depicting a second alternative baffle design.

While FIGS. 1-6 depict brushes, examples of baffling also include, and are not limited to singularly or in concert, rotating brushes, fixed brushes, baffling plastic material, or foam. An alternate design of a baffle to contain germicidal light is shown in FIGS. 25A and 25B. In FIGS. 25A and 25B, a cross section of a sterilization machine is shown. In FIG. 25A, the machine has baffles 100 that angle outward, projecting away from the exterior of the machine. The machine has an inner top 102, back 101, bottom 103, and a germicidal light source 104, such as a UV laser, UV lamp, UV light emitting diode, and so forth. In FIG. 25B, the baffles 105 angle inward, projecting towards the back of the machine. These baffles 100, 105 may be made of a stiff material (e.g., metal, or hard, rigid plastic) or a flexible material (e.g., foam, soft plastic), or a combination thereof. In either embodiment, or standing alone, a UV absorbing or reflecting fabric, plastic, or foam draping, covering, or sheathing may also be used to help cover the opening if desired.

The alternate baffle design uses a placement of reflective and nonreflective surfaces on the interior portions of the baffles so as to only allow a minimal amount of light to exit the front of the machine. Where the back of the machine is made to be less or non-reflective to UV light combined with an angled front baffle that is reflective, the machine can contain a sufficient amount of light within itself to maintain safe operation. This may often be beneficial since the baffle would not have to make contact with the surface of the gloves which may decrease the wear of the baffling element and decrease a potential source of contamination. FIG. 25 shows side view of two different embodiments of a sterilizing machine with a reflective baffle.

Continuing with FIG. 3, The flash tube assembly 20 is electrically connected to the controller 18. The flash tube assembly 20 serves as a germicidal light source and emits light in the germicidal spectrum. Examples of the types of light sources that may be incorporated into this embodiment include but are not limited to a xenon arc lamp, xenon flash lamp, low pressure lamp, medium pressure lamp, light emitting diode, laser, or other light emitter capable of emitting light in the disinfecting UV spectrum. The controller 18 may also include but is not limited to a flash triggering driver capable of powering a flash lamp, a ballast capable of lighting low or medium pressure lamps, a drive board capable of turning on the light emitting diode, a constant current driver board capable of driving a laser, and/or a drive board capable of driving a light emitter capable of emitting light in the disinfecting UV spectrum. In some embodiments, multiple UV light sources such as two, three, four, or a series of light emitting diodes; two, three, four, or more lamps; two, three, four, or more lasers; or a combination of any of the foregoing, either as primary or as backup UV light sources.

Figure 4:
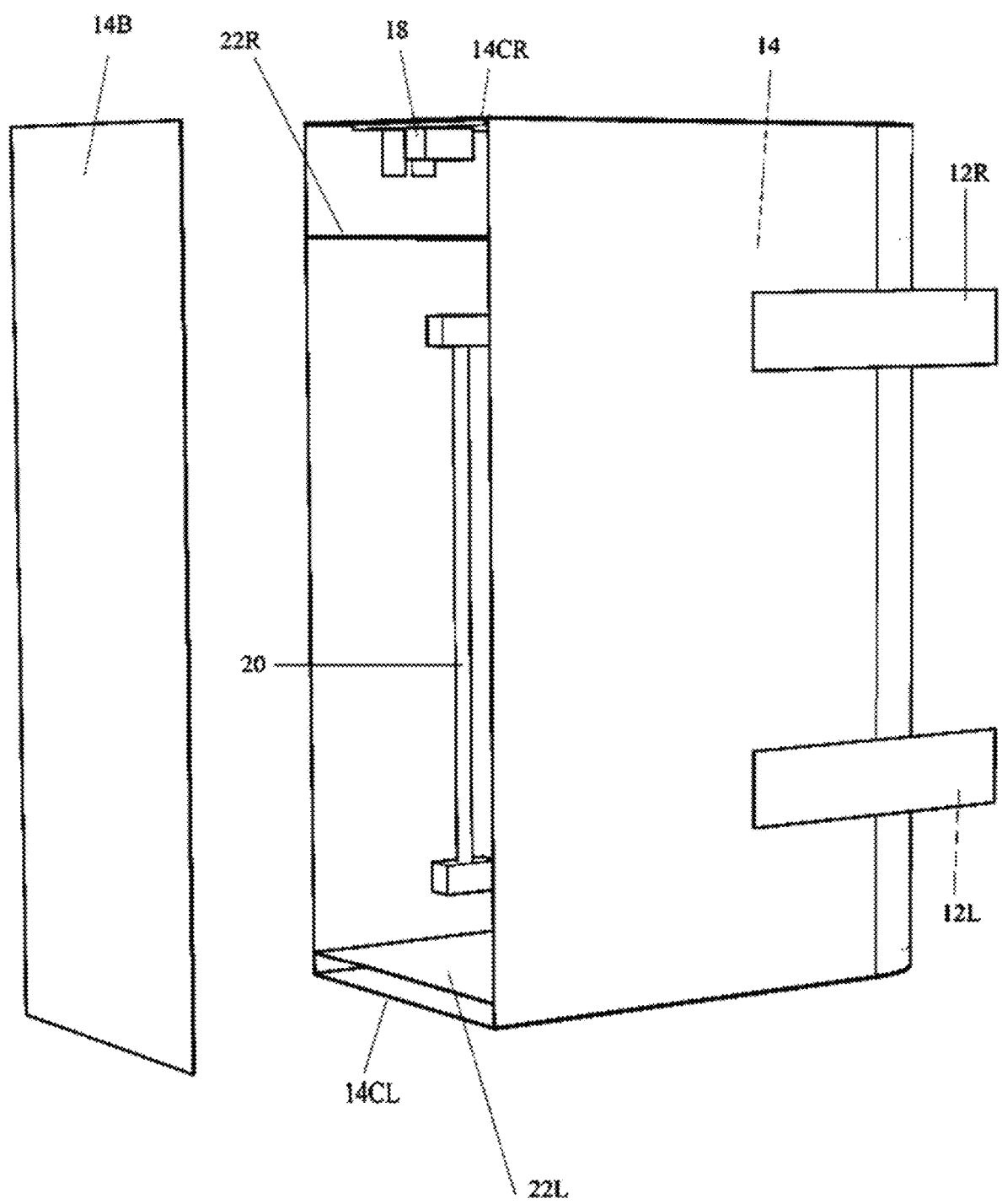
FIG. 4 depicts a top view of another embodiment of a sterilizing machine with the back panel removed, depicting photoelectric sensors and the back panel.

In FIG. 4, the body assembly has subcomponents, right cover 14CR, left cover 14CL, and back cover 14B that are all connected in a rectangular prism shape. Covering the controller 18, right end of the brushes 10B and 10T (not shown), and drive assembly 16, is the right interior cover plate 22R. On the inside of the left cover 14CL is the left interior cover plate 22L. On the top and bottom of the machine, the body assembly 14 has two arced sections that follow the path of the brushes when one bristle section is parallel to the front of the machine. On the top of the body assembly 14 are mounted two photoelectric sensors 12L and 12R that are positioned in such a way to sense hand coverings entering the machine. The photoelectric sensors 12L and 12R are wired to the controller 18 which will typically not allow the activation of the flash tube assembly 20 unless the hand coverings are in an optimal position. One of the potentially optimal positions is one that allows the touching surfaces of the hand covering to be exposed to as much germicidal light from the flash tube assembly 20 as possible, while ensuring that no unprotected body parts are exposed to the germicidal light.

The controller 18 has wiring to communicate with, or to receive input from, the photoelectric sensors 12L and 12R in order to determine the optimal hand depth, typically activating the germicidal light source when it is safe to do so. The controller 18 may be mounted inside or outside of the prism body assembly 14. When the controller 18 is mounted inside the assembly 14, a cover may be used to protect the circuits from ultraviolet radiation. While FIGS. 1-6 depict photoelectric sensors 12L and 12R, other types of sensors contemplated in the embodiments include but are not limited to a mechanical backstop with touch sensor(s), photo electric sensor(s), foot pedal(s), ultrasonic sensor(s), hall effect sensor(s), or digital camera(s).

The hand coverings may have a high contrast, machine readable pattern, distinct from the hand covering, that is placed in such a way to correspond to the optimal hand insertion depth for the sterilization machine for a specific size of hand covering. One embodiment of the sensor mechanism/circuit would sense the optical position of the high contrast pattern on the hand coverings before allowing the light, flash, led, laser, or light emitter to activate.

Figure 5:
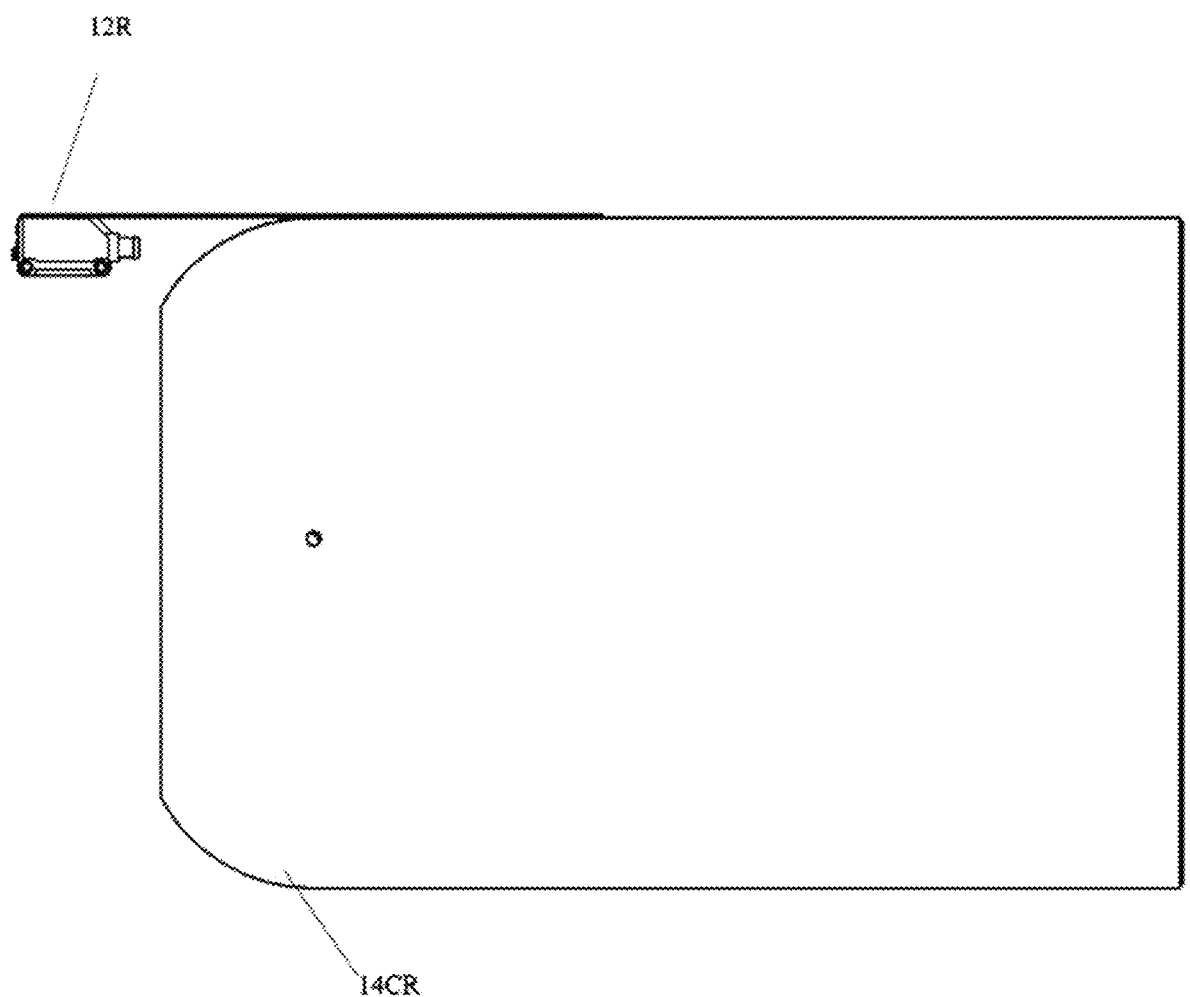
FIG. 5 depicts a side view of a sterilizing machine sitting flat.
Figure 6:
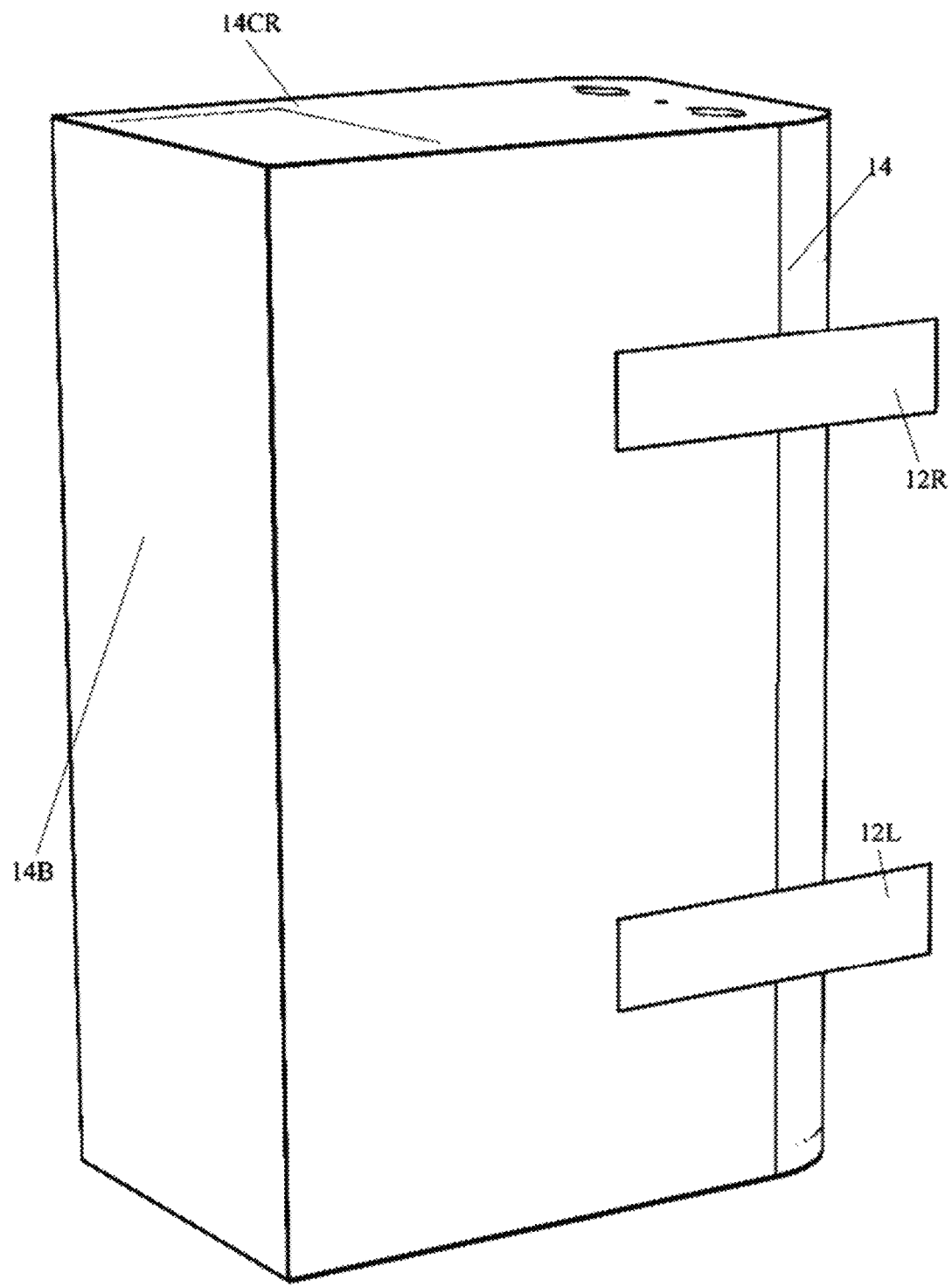
FIG. 6 depicts a top view of a sterilizing machine.

In FIG. 5, a side view of a sterilizing machine sitting flat is depicted with photoelectric sensor 12R and right cover 14CR. In FIG. 6, a top view of a sterilizing machine is depicted with back cover 14B, right cover 14CR, body assembly 14, and photoelectric sensors 12L and 12R.

In some embodiments, the bafflings will rotate or be exposed to the germicidal light without hand coverings inserted after each treatment to decrease cross contamination further. When using rotating baffling elements, the element may rotate to expose a different baffling surface after each treatment to allow for the previously used surface to be disinfected before being used again. This can be exemplified by the rotating brushes depicted in FIG. 1.

Figure 7:
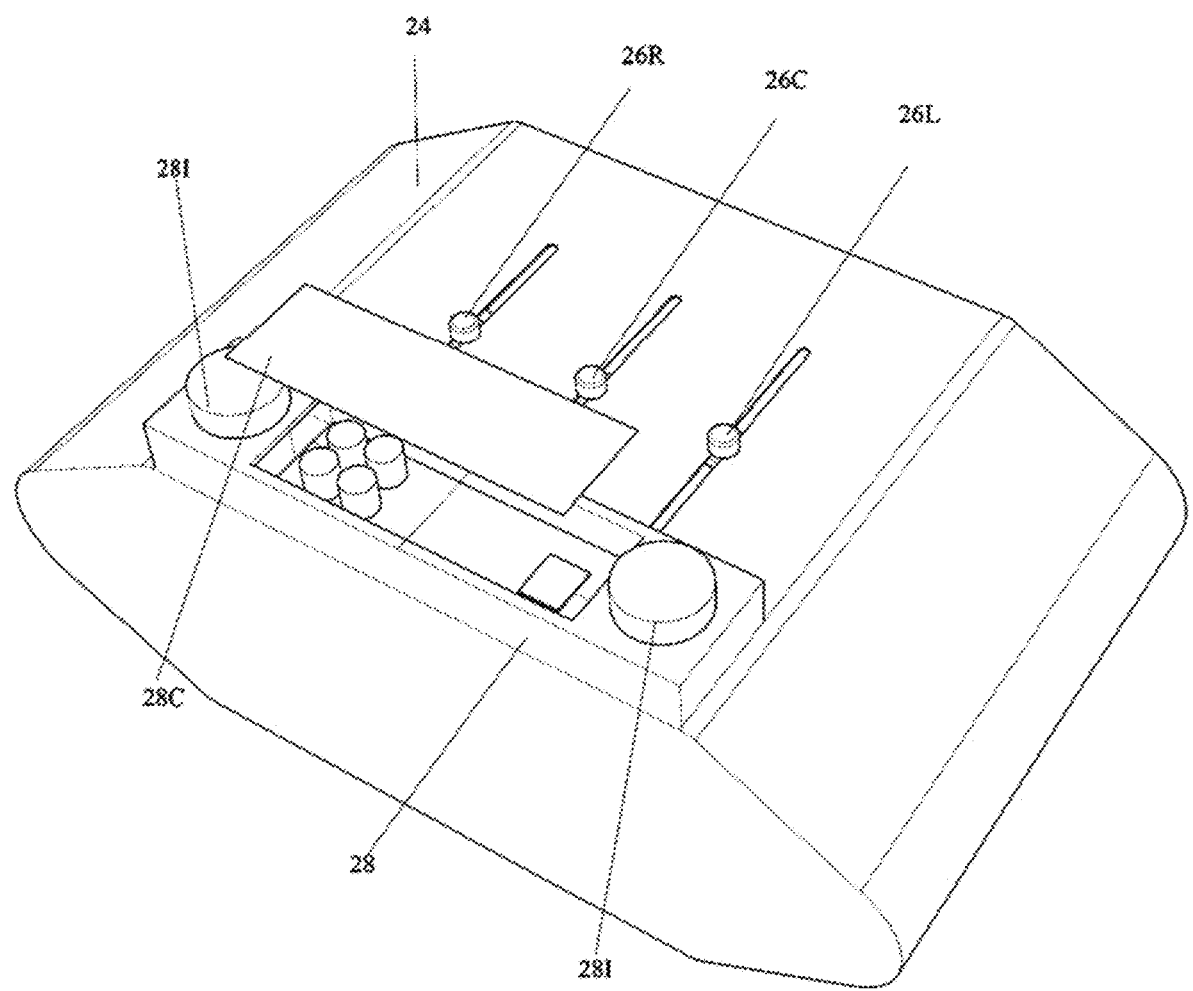
FIG. 7 depicts a perspective view of the back of a second embodiment of a sterilizing machine.

A second embodiment of a sterilizing machine is shown in FIGS. 7-10, similar to the first and embodiment, but with various modifications. In FIG. 7, an embodiment of the sterilization machine is formed by an enclosure 24 that is shaped in a hexagonal prism shape. The enclosure 24, has a section that allows for the adjustable mounting of a touch sensitive backstop 34 (not shown). The touch sensitivity of the backstop 34, may be implemented through, non-exclusively, a micro switch or switches, piezo electric sensor(s), optical sensor(s), or capacitive sensor(s). In cases where a backstop is used to sense the presence of hands, adjusting screws 26R, 26L, and 26C permit the backstop to be adjusted so as to accommodate the appropriate depth.

Alternatively, the sterilization machine may be activated by an external sensor or switch including but not limited to a foot pedal. The sensor or switch is electrically connected to the controller 28. The enclosure 24 houses a low-pressure ultraviolet lamp 32 (not shown) in such a way to contain all, or effectively all, of the light emitted by the lamp. The lamp is electrically connected to the controller 28. The controller 28 is fixed to the enclosure 24. The controller may also have a cover 28C, the removal of which allows access to the controller's internal parts. The controller 28 can be implemented with indicating lights 28I as a visible indication to customers of when gloves are cleaned. The enclosure 24 has openings for hands to be inserted that will be covered by baffling material 30 (not shown). In some embodiments, multiple UV light sources such as two, three, four, or a series of light emitting diodes; two, three, four, or more lamps; two, three, four, or more lasers; or a combination of any of the foregoing, either as primary or as backup UV light sources.

Figure 8:
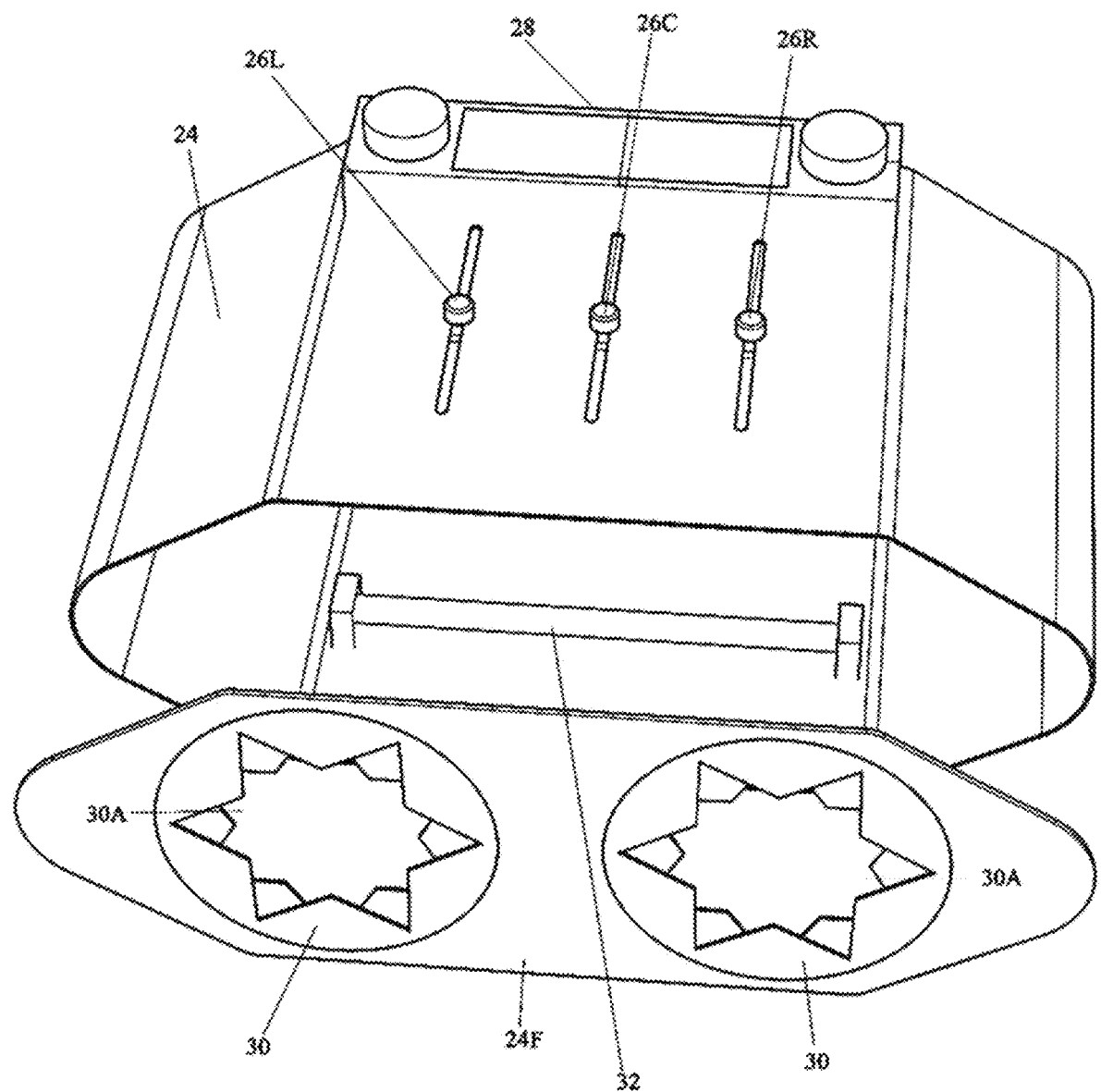
FIG. 8 depicts a perspective view of the front of a second embodiment of a sterilizing machine with the front panel removed, showing hand baffles.
Figure 9:
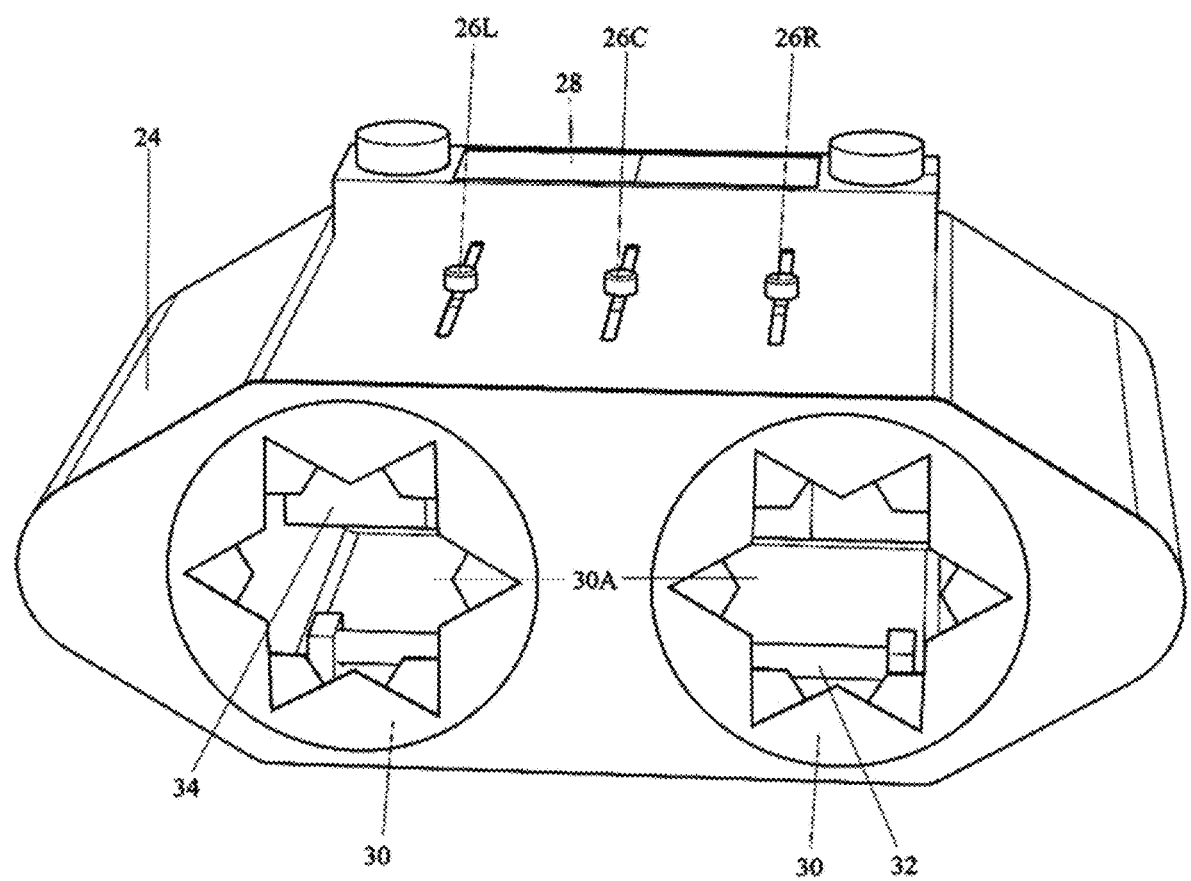
FIG. 9 depicts a front view of a second embodiment of a sterilizing machine, showing a front panel installed and hand baffles.
Figure 10:
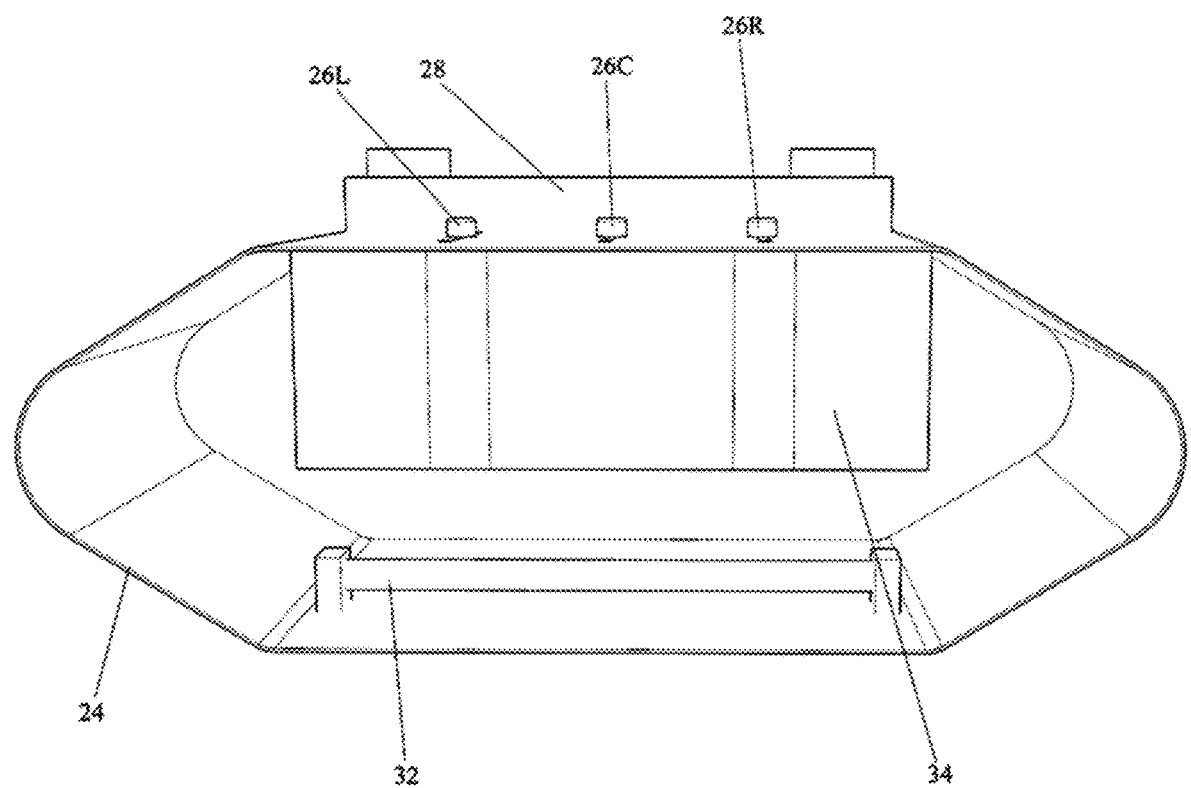
FIG. 10 depicts a front view of a second embodiment of a sterilizing machine, without a front panel or hand baffles.

In FIG. 8, a perspective view of the front of the sterilizing machine is shown, with the front panel 24F removed, depicting the hand baffles 30A and baffling material 30. In FIG. 9, a front view of the sterilizing machine, showing a front panel 24F installed. In FIG. 10, a front view is shown of the sterilizing machine, without a front panel 24F or hand baffles 30A, but with the backstop 34 more visible.

Figure 11:
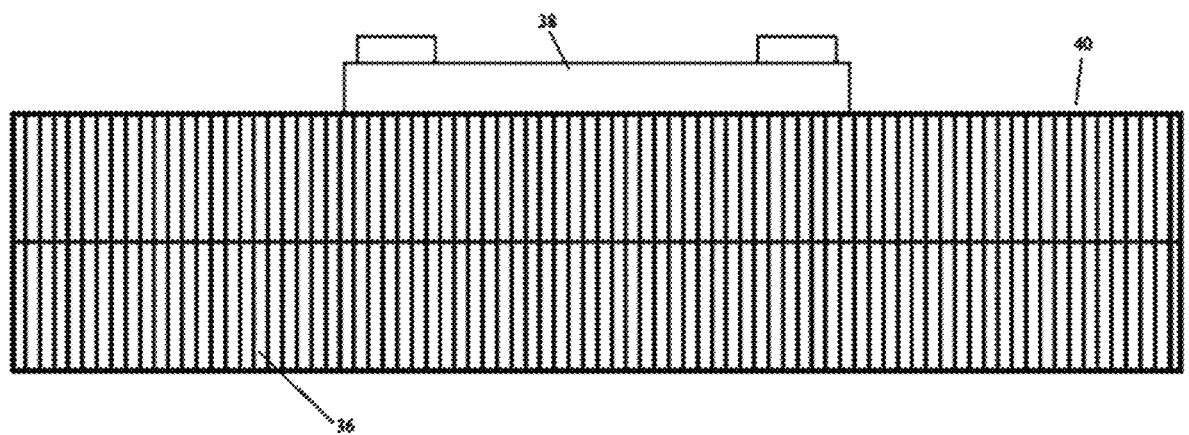
FIG. 11 depicts a front view of a fully assembled third embodiment of a sterilizing machine.

FIGS. 11-14 depict a third embodiment of a sterilization machine, similar to the first and second embodiments, but with various modifications. In FIG. 11, a front view of a fully assembled sterilizing machine is shown. The machine is formed from an enclosure 40 that is shaped as a rectangular prism with an opening covered by flexible materials, here, front sealing foam pieces 36 that have small gaps and are attached to the sterilization machine so as to block all, or effectively all, ultraviolet light from exiting the enclosure to the exterior environment surrounding the machine. Other flexible, stationary materials such as fibers, fabrics, stiff ropes or cords, bristles, strands, drapes, plastic or rubber pieces, and/or other flexible protruding or hanging material may be used instead of or in addition to foam pieces. Anti-microbial coatings may also be applied to, or integrated into, the foam pieces or other stationary materials. A controller 38 has an appropriate driver to trigger the light source when the gloved hands are placed into the optimal position.

In each of the first, second, and third embodiments discussed above, as well as those hereafter, power for a sterilizing machine may be provided by typical AC power from a typical residential outlet. Additionally, or in the alternative, the sterilizing machine may also contain a battery such as a lithium-ion or nickel-metal hydride battery. This facilitates use in emergency environments or where an AC power source is unavailable or inconvenient.

In some situations, a UV light source may experience more wear from cycling on and off than if the UV light source was left on for an extended period of time. Such UV light sources may include medium and low-pressure mercury lamps. In such cases it may be beneficial to avoid cycling on and off the light source while still ensuring safety. This can be done by leaving the lamp on in a low-power or safe-power mode.

One safety measure that may be used with a UV light source is an optical sensor to determine if a hand is approaching or inserted into the machine. The safety conditions of the gloves may then be checked using the distinctive mark on the gloves prior to the hand fully entering the sterilizing machine. An exposed hand may be detected by checking the color and shape of the glove. The light source may be turned off if the gloves (or an ungloved hand) trigger an error condition. The error would then need to be resolved and the machine sterilizing machine reset. Mark placements on the gloves on the fingers, or on the tips of the fingers, allow for optical sensors to detect an issue more quickly so that improperly protected hands do not get exposed to the light source.

Figure 12:
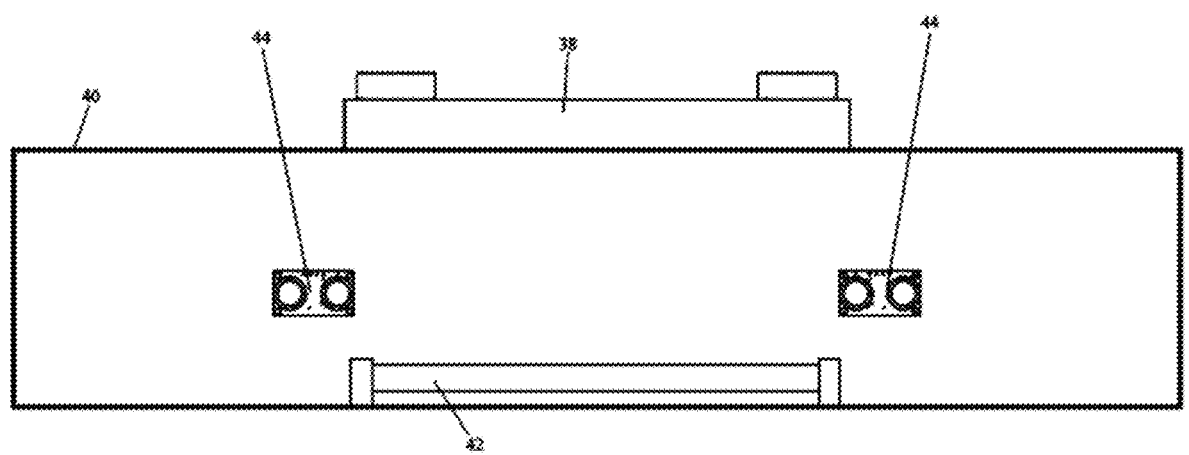
FIG. 12 depicts a third embodiment of a sterilizing machine without front sealing foam pieces, showing a bar shaped ultraviolet light emitter such as a laser.
Figure 13:
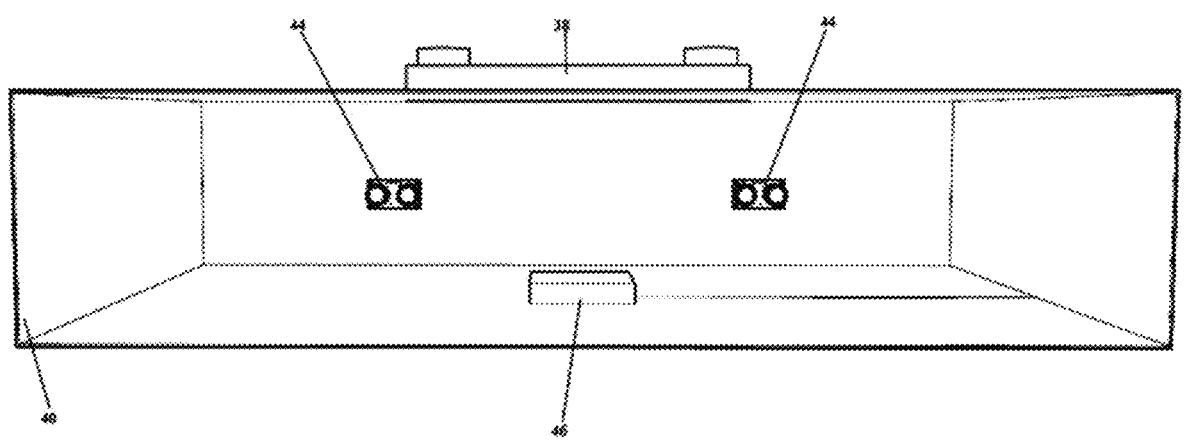
FIG. 13 depicts a front view of a third embodiment of a sterilizing machine without front sealing foam pieces, showing an ultraviolet light emitter such as a diode.
Figure 14:
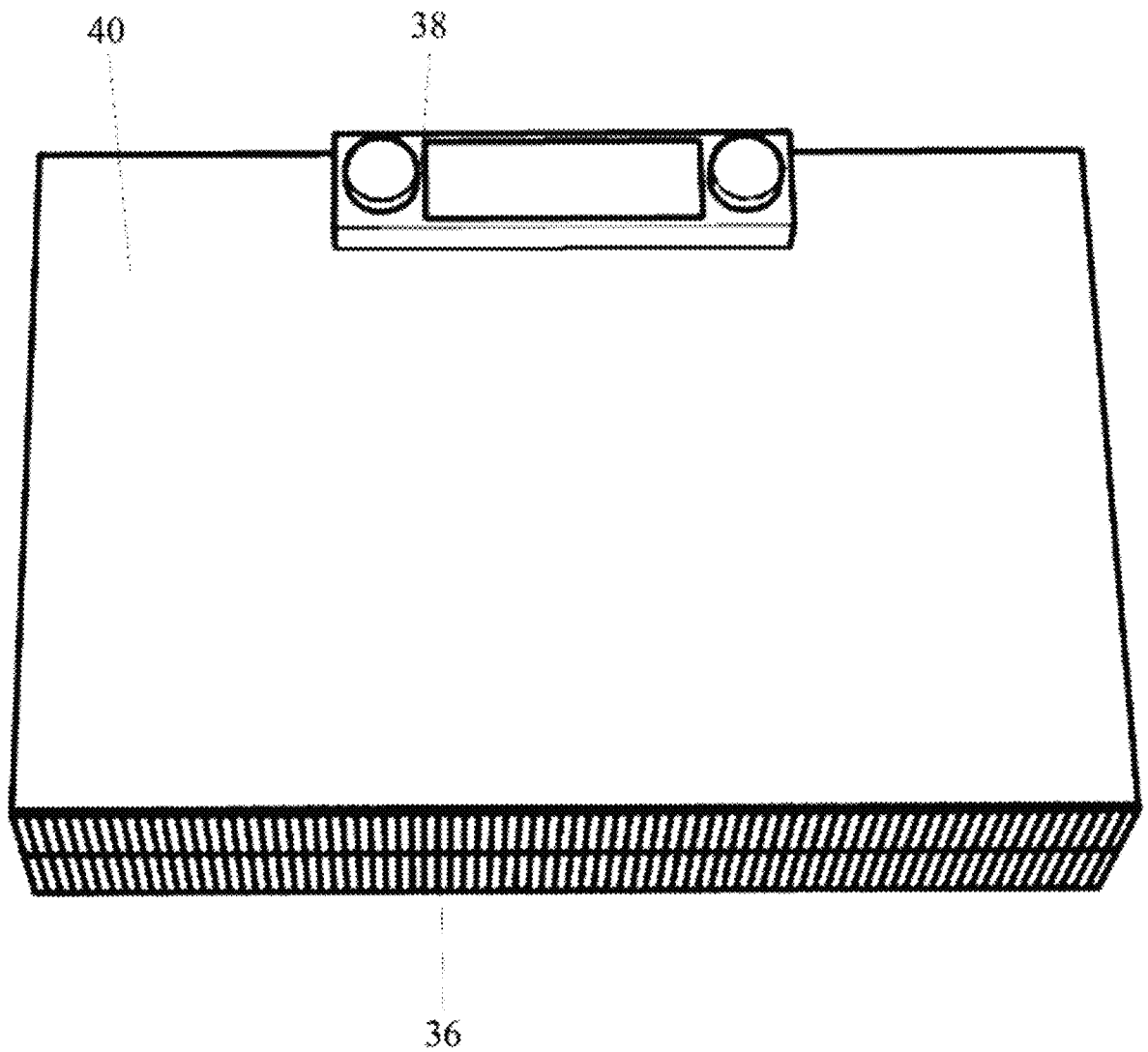
FIG. 14 depicts a top view of a third embodiment of a sterilizing machine.

FIG. 12 shows a sterilizing machine with an enclosure 40 but with front sealing foam pieces removed. A bar shaped ultraviolet light emitter is visible, in this embodiment a laser 42. Distance sensors 44 (such as optical, photoelectric, or ultrasonic sensors) detect proper hand depth and provide signals to the controller 38. In FIG. 13, a front view of the sterilizing machine is shown with the front sealing foam pieces 36 removed, revealing an ultraviolet light emitter, here a diode 46. In FIG. 14, a top view of the sterilizing machine is shown. In some embodiments, multiple UV light sources such as two, three, four, or a series of light emitting diodes; two, three, four, or more lamps; two, three, four, or more lasers; or a combination of any of the foregoing, either as primary or as backup UV light sources. These light sources are typically mounted in an optimal position to expose the touch surfaces of the hand coverings. As with other embodiments, the optical and distance sensors (e.g., items 12L, 12R, and 44) may be replaced and/or supplemented with digital camera(s) and/or barcode readers.

Before gloved hands or hand coverings should be inserted into the sterilization machine, one or more factors may be verified so as to allow for safe exposure. A first criteria may be that the hands are gloved. If a sterilizing machine was only to be used infrequently (e.g., less than 10 times per day), ungloved hands might not be a problem as the total exposure to the skin would be minimal and potentially safe. In other use cases, a service person's hands will be dosed many orders of magnitude higher (for example through increased light intensity per cleaning, increased exposure time per cleaning, and/or repeated application) such that exposure to the skin will surpass safe levels. Gloves may be a requirement in some use cases, most often when the device is used frequently.

A second criteria may be that the glove type is the correct type to absorb, block, or reflect enough ultraviolet light to sufficiently protect the hands. Different types of common disposable gloves greatly differ in transmittance of ultraviolet light. The article titled "Determination of the Attenuation Properties of Laboratory Gloves Exposed to an Ultraviolet Transilluminator", published in *the Journal of Occupational and Environmental Hygiene*, explained that the average UVA percent transmittance using the radiometer method with an unstretched glove was 73.7%, 0.17%, and 1.12% for vinyl, nitrile, and latex, respectively. The average actinic percent transmittance for an unstretched glove was 13.6%, 0.011%, and 0.011% for vinyl, nitrile, and latex, respectively. [Gazdik, Edward et al. "Determination of the Attenuation Properties of Laboratory Gloves Exposed to an Ultraviolet Transilluminator." *Journal of Occupational and Environmental Hygiene* vol. 1:6. Pages 391-402. 17 Aug. 2010, doi: 10.1080/15459620490452013]. It is important to note that while latex gloves may have had a lower actinic percent transmission than latex gloves, the latex gloves tested were significantly thicker than the nitrile gloves tested, which may have a significant impact on transmission. While UV-A has high exposure allowances for the skin, when used in cases with very high frequency, it may still be an important safety consideration. Actinic transmission is of greater importance when considering safety. The differences between the transmittance are significant and may have a large impact on safety. Vinyl gloves might allow too much transmission of ultraviolet light for some, but not all, low-frequency use cases. Latex gloves may be suitable for some, but not all, medium or high frequency use cases, since they have the lowest actinic transmission, but they allow for a relatively large portion of UV-A when considering the cumulative exposure to the hands through the gloves. Latex allergies also may make it difficult for latex gloves to be standardized.

Nitrile gloves may in some cases provide ideal characteristics allowing for low UV-A and actinic UV transmission for lower thicknesses, but in use cases where a higher dose is desired for each treatment, nitrile gloves may still allow for too much exposure. To combat this, and depending on the use case, additives may be used in the nitrile mix (as well as other glove rubber or polymer mixes) such as carbon pigmentation or other ultraviolet absorbing or reflecting compounds. Gloves may also be coated in a metallic coating which may also improve the protection provided at the tradeoff of potentially increased cost. A thin reflective coating may be applied to the surface of the gloves to reflect either UV-B or UV-C wavelengths more to provide greater protection to the skin or increase the effectiveness of the germicidal light.

A third criteria may be the glove manufacturer, model, materials, and/or information inferred therefrom. Various formulations of glove materials may provide very different ultraviolet transmissive characteristics, as such, information concerning the manufacturer, glove model, or specific glove materials may be desirable to know so that it can be determined whether the gloves have sufficient ultraviolet blocking characteristics.

A fourth criteria may be the cumulative ultraviolet exposure of the glove. Gloves that have been exposed to high levels of ultraviolet may begin to decrease in elasticity or may break without a service person noticing, allowing for bare skin to be exposed to the ultraviolet light and/or permitting skin to come into contact with customers or items the customer interacts with. In other words, after each treatment, the gloves may potentially degrade or experience a change in properties, and this may be accounted for.

A fifth criteria may be the age of the gloves. Gloves may decrease in elasticity with age which may lead to unnoticed breakages and ultraviolet exposure. This also may be accounted for.

A sixth criteria may be the time that the gloves have been worn. As gloves are used, they may stretch over time. When gloves are stretched, they may transmit more ultraviolet light due to the reduced thickness or fracturing of the material. The amount of stretching that occurs with normal use depends on the formulation of the glove materials and the amount of time it is used for. A situation where an employer requires his employees to reuse gloves may lead to dangerous or even harmful exposure levels. Alternatively, some employees may try to use gloves for an extended period of time, or simply avoid changing them so as to be more time efficient.

A seventh criteria may be whether only the gloved portion of a hand, wrist, or arm is exposed. To ensure that skin that is uncovered by the right kind of glove is not exposed various measurements may be taken. The depth of the hand into the machine may in some cases be an important measure. Sensing or estimating skin exposure helps to ensure that no, or minimal, ungloved skin passes through a baffle or is otherwise exposed to UV light.

Other factors complicate this process. For instance, the angle of the hands entering the machine may allow for repeated exposure of the skin to ultraviolet light. Alternatively, sensors may not actually be measuring the position of the glove but may instead be measuring other items on the arm such as watches, jewelry, or sleeves. Any of these or other errors might allow for repeated exposure of unprotected skin and may have dangerous consequences. A service person may not notice that one of these factors is causing them to insert unprotected skin past the baffle and might continue using their technique for a prolonged period of time. In some cases, a single shift (or even a single exposure) may provide a high enough dose of ultraviolet radiation to cause lasting damage. Additionally, a wrong technique that exposes the skin can quickly become habitual, leading to daily excessive or harmful exposure.

Figure 19:
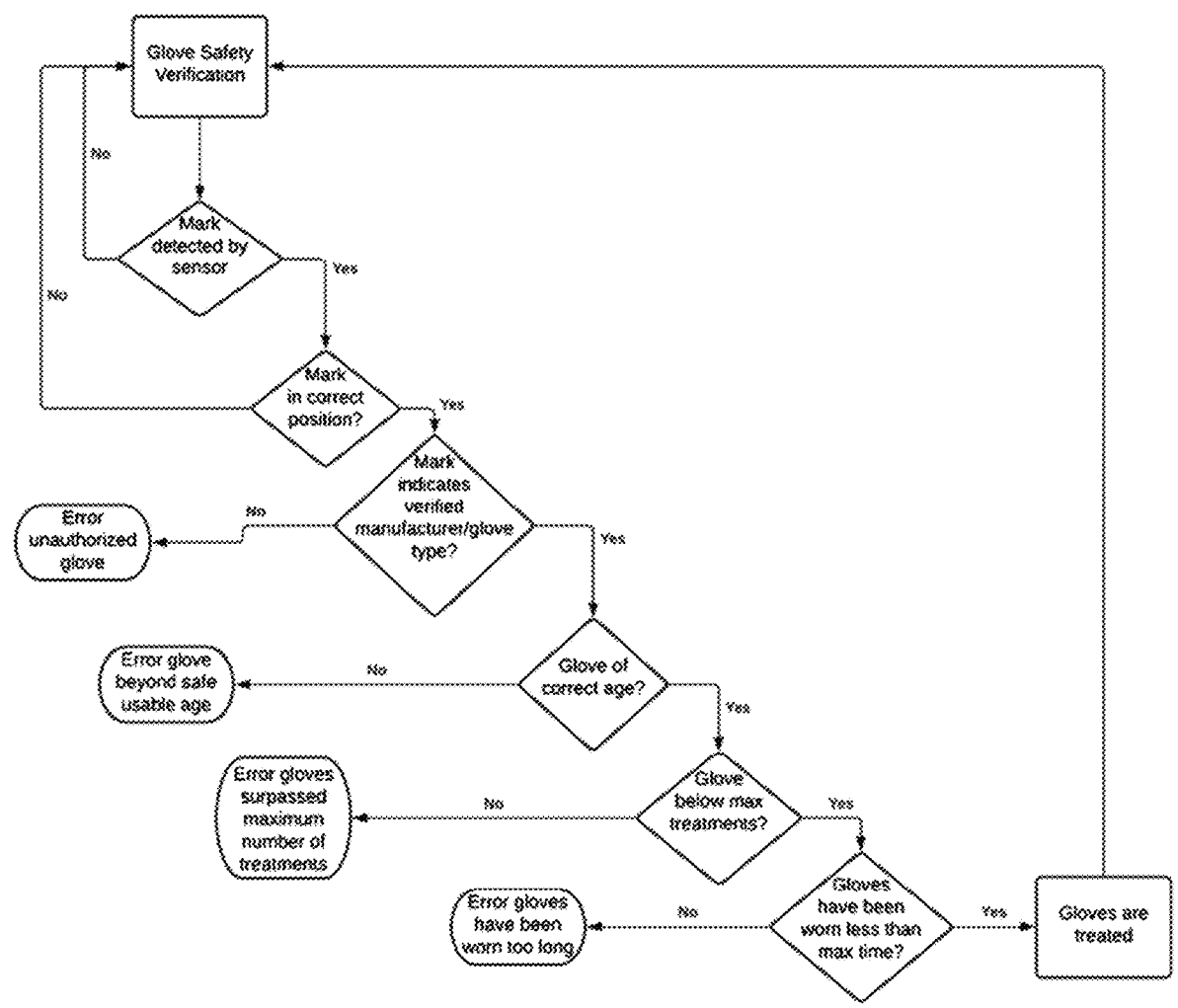
FIG. 19 depicts a process that verifies sanitization of a specialized hand covering in a sterilizing machine by analyzing numerous safety factors.

FIG. 19 shows a glove safety verification process by which each of these safety criteria may be analyzed using information encoded into the gloves. To be able to maintain safe operation of an ultraviolet treatment of hand coverings, the system can verify one or more or all of the above-mentioned criteria (in the same order presented or a different order) before emitting ultraviolet light. A distinguishing mark on the hand coverings (discussed below) may be used to provide the system with some or all of the information required in FIG. 19. In FIG. 19, the process must verify all criteria before the gloves are treated. If a criterion cannot be verified, then the system enters an error state, which may be temporary, manually resettable, and/or self-clearing, or in some cases permanent until a higher authority (e.g., a supervisor) resets it. Once reset, the process begins again. Alternatively, if one or more criteria cannot be verified, or exceed or fall below a certain threshold or state, or differ in some quantity or context, and/or simply fail, a lesser dose or dose duration may be administered.

FIGS. 15-18 are embodiments of various distinguishing marks that can be used on the hand coverings. A single (or multiple) identical mark(s) may be on both gloves, different mark(s) may be on both gloves, or a single mark (or multiple marks) may be on one single glove.

Figure 15:
FIG. 15 depicts an embodiment of a specialized hand covering.

In FIG. 15, an embodiment of a simple distinguishing mark 50 on a hand covering is shown. The mark may vary in complexity and form. A simple mark such as a high contrast line, shape, pattern, or other distinguishing visual, machine readable feature may be used in conjunction with optical sensors on the sterilization machine to safely activate the germicidal light source. The mark may also be a specialized reflective material that is detected by one or more optical sensors. This use of a mark may also be licensed to verified manufacturers that meet all the standards required for the safe operation of the sterilization machine.

Figure 16:
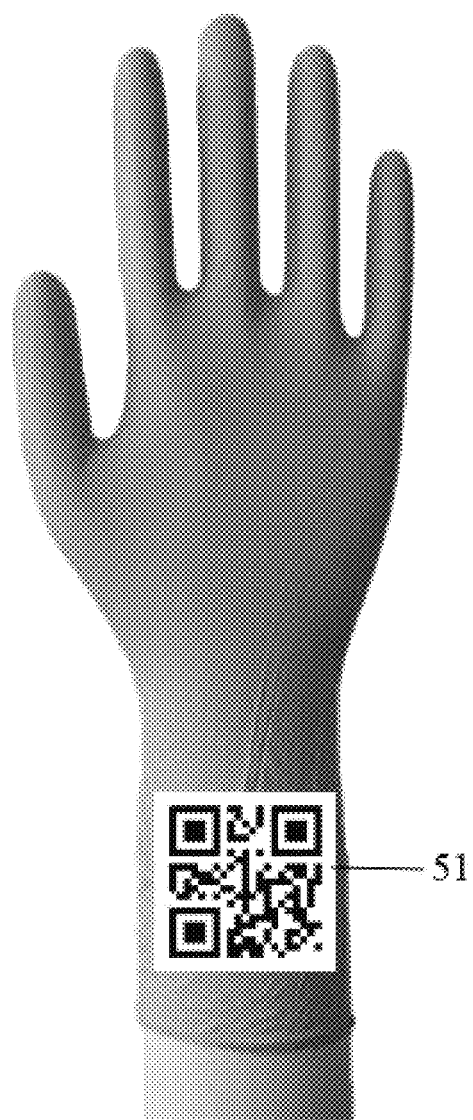
FIG. 16 depicts a second embodiment of a specialized hand covering with high contrast marking.
Figure 17:
FIG. 17 depicts a third embodiment of a specialized hand covering with high contrast marking that uses different colors for identification purposes.

FIG. 16 and FIG. 17 show more complex marks 51 and 52 respectively, that allow for each hand covering to be identified individually or as a pair. The controller of the sterilizing machine in some cases may only allow the machine to work with some specific number of hand coverings that a customer has purchased. Alternatively, microchips may interface with the controller to provide criteria information, or a magneto strictive device and/or magnets imbedded into the coverings may also provide criteria information with respect to the glove. More complex marks may also be able to directly store or indicate data or criteria information. Some examples of more complex marks include, but are not limited to, QR codes (a preferred embodiment), bar codes, color-based codes, serial numbers, unique patterns, and/or the combination of a simpler mark with a unique designator for each glove.

More complex markings allow for each individual glove (or a pair of gloves) to store or link to data about the characteristics of the glove such as manufacturer, verification of standards, age of glove, the time a glove has been used, the number of treatments a glove has undergone, or other characteristics. This data may be stored on an external server and may be updated, directly or indirectly, by a sterilization machine. In some embodiments, the sterilization machine's controller is a network server that communicates with the sterilization machine using a network interface such as wired ethernet or Wi-Fi. The position of these complex marks may be determined with one or more optical sensors on a sterilizing machine. To further verify the authenticity of the origin of a glove and its safety standard, cryptographic signatures can be used with these more complex marks so that these characteristics can be definitively verified.

The high contrast marking in FIGS. 15-17 are typically suited to sterilizing machine embodiments that use optical sensors such as a camera or a photoelectric sensor. Implementations of markings may include barcodes or QR codes shown in FIG. 16, or a special color code shown in FIG. 17. Other implementations of verifying authenticity may include but are not limited to an RFID tag embedded in the hand covering or magneto strictive devices that emit identifiable signatures with corresponding sensors built into the sterilizing machine to detect that the proper coverings are being used and/or that the desired criteria have been met.

In some circumstances, a scanner (for example, a barcode reader or a digital camera) may be used in place of the sterilization machine to scan the user's hand coverings. In such an embodiment, the scanner may communicate with a networked server that connects both to the scanner and the user's indicator device. In one embodiment, the user's gloves are scanned by the scanner. The scanner forwards the information encoded on the gloves to networked server. The server examines the glove information to determine whether the gloves should be changed in light of various factors such as the user having been located in an area requiring a glove change (e.g., a rest room), the amount of time elapsed since the gloves were last scanned, the amount of time elapsed since the gloves were put on, and/or other factors. The server then may provide an update to the user's indicator device, or to a visual or auditory output on the scanner, as to whether the gloves should be changed. The markings on the gloves may also serve to change the way the sterilization machine functions. Different types of gloves can have different marks such that the sterilization machine sets the treatment level such as power, wavelength, energy, and/or duration to some predetermined or calculated amount. This may be beneficial in some use cases as different applications may require different amounts of pathogen reduction or inactivation. For instance, a medical use case would require a very high level of pathogen reduction while a cashier at a store would not necessarily need to have their gloves cleaned as thoroughly. When a different treatment level is used, different gloves may be used to optimize user protection and/or cost. It may be more expensive to create gloves with higher levels of protection, so segmenting glove types for different use cases may in some cases help ensure that costs are a low as possible for a specific use, while still providing adequate protection and sterilization.

To demonstrate the effects of glove type for different light sources, UV-C target dosage, and that skin exposure is limited, calculations were made to find the maximum number of treatments to the surface of the gloves that does not exceed safety standards. The unprotected skin limit for total actinic UV-B and UV-C radiation exposure given by the ACGIH TLV booklet [American Conference of Governmental Industrial Hygienists. Ultraviolet Radiation: TLV® Physical Agents 7th Edition Documentation] is 3 mJ/cm^2 and was used as the upper limit for the glove exposure calculations in Tables 1-3 below. This limit may be conservative and perhaps the upper safe limit is higher. While UV-C transmission through gloves may still be worth considering, the data used for the transmission of different wavelengths of light through gloves appears to suggest that very little UV-C is transmitted through any glove material, while glove materials typically have a much higher UV-B transmittance. This suggests that to calculate the maximum number of gloved hand exposures to UV radiation, both the parts of the UV light spectrum emitted as well as the glove transmission for each part of the UV spectrum should typically be taken into consideration.

To estimate the UV-B output of various light sources, the amount of UV-B energy for every unit of UV-C energy was determined by comparing relative intensities on a spectrometer. Such estimates are useful to show that the composition and type of glove can be an important safety concern. For a low-pressure mercury lamp, it can be estimated that a value of energy 2% of the UV-C energy output is emitted in the UV-B range. For a medium pressure mercury lamp, it can be estimated that a value of energy 130% of the UV-C energy output is emitted in the UV-B range. For a xenon flash lamp, it can be estimated that a value of energy 60% of the UV-C energy output is emitted in the UV-B range. An LED's output in the UV spectrum varies widely among manufacturers and typically their specifications may be relied upon absent independent testing. Lasers are typically narrowly focused on only their specified wavelength.

All of these measures may vary with configuration and manufacturer and may in some cases actual transmission through the glove may need to be calculated using other techniques, such as directly testing transmission through the preferred glove type for each wavelength. Some of the glove transmission percentages may be found in measurements from the article titled "Determination of the Attenuation Properties of Laboratory Gloves Exposed to an Ultraviolet Transilluminator" found in the *Journal of Occupational and Environmental Hygiene*

To calculate the maximum number of treatments, the limit for actinic UV exposure was divided by the UV energy output and then multiplied by the glove actinic transmission rate. Note that for some jobs such as security personnel at airports or train stations, the number of treatments in a single shift may total in the thousands. The UV-C doses for which these conditions were calculated also may be significantly higher if it was wanted or necessary. It is also important to note that the required UV-C dose to kill or inactivate pathogens is often lower in sources that emit more UV-B due to the action of UV-B to kill or inactive pathogens or to amplify the effects of UV-C.

Table 1 is a reference for a low-pressure mercury lamp, and the table provides a comparison of a glove type and a UV-C dosage in mJ/cm2, estimates the corresponding UV-B dosage, and provides a maximum number of treatments for that corresponding glove type such that the total skin exposure to UV-B is less than 3 mJ/cm2. The vinyl, latex, and blue nitrile numbers were gathered from Attenuation Properties of Laboratory Gloves Exposed to an Ultraviolet Transilluminator" found in the *Journal of Occupational and Environmental Hygiene*. The black nitrile and black high carbon nitrile numbers are estimates based on thickness and carbon absorption data. Table 2 and Table 3 are corresponding references for a medium pressure mercury lamp and a xenon flash lamp, respectively.

TABLE 1

Maximum Allowable Number of Treatments for Various Glove Types Using Low Pressure Mercury Lamp.

| Glove Type | UV-C Dose (mJ/cm^2) | UV-B Dose (mJ/cm^2) | Max Treatments |
|---|---|---|---|
| None | 15 | 0.3 | 0 |
| None | 40 | 0.8 | 0 |
| Vinyl | 15 | 0.3 | 75 |
| Vinyl | 40 | 0.8 | 28 |
| Latex | 15 | 0.3 | 66,666 |
| Latex | 40 | 0.8 | 25,000 |
| Nitrile - Blue 5 mil | 15 | 0.3 | 41,666 |
| Nitrile - Blue 5 mil | 40 | 0.8 | 15,625 |
| Nitrile - Blue 5 mil | 100 | 2 | 6,250 |
| Nitrile - Black 7 mil | 15 | 0.3 | 83,333 |
| Nitrile - Black 7 mil | 40 | 0.8 | 31,250 |
| Nitrile - Black 7 mil | 100 | 2 | 12,500 |
| Nitrile - Black 9 mil | 15 | 0.3 | 104,166 |
| Nitrile - Black 9 mil | 40 | 0.8 | 39,062 |
| Nitrile - Black 9 mil | 100 | 2 | 15,625 |
| Nitrile - Black 7 mil High Carbon | 15 | 0.3 | 166,666 |
| Nitrile - Black 7 mil High Carbon | 40 | 0.8 | 62,500 |
| Nitrile - Black 7 mil High Carbon | 100 | 2 | 25,000 |
| Nitrile - Black 9 mil High Carbon | 15 | 0.3 | 250,000 |
| Nitrile - Black 9 mil High Carbon | 40 | 0.8 | 93,750 |
| Nitrile - Black 9 mil High Carbon | 100 | 2 | 37,500 |

TABLE 2

Maximum Allowable Number of Treatments for Various Glove Types Using Medium Pressure Mercury Lamp.

| Glove Type | UV-C Dose (mJ/cm^2) | UV-B Dose (mJ/cm^2) | Max Treatments |
|---|---|---|---|
| None | 15 | 20 | 0 |
| None | 40 | 53 | 0 |
| Vinyl | 15 | 20 | 1 |
| Vinyl | 40 | 53 | 0 |
| Latex | 15 | 20 | 1,000 |
| Latex | 40 | 53 | 375 |
| Nitrile - Blue 5 mil | 15 | 20 | 625 |
| Nitrile - Blue 5 mil | 40 | 53 | 234 |
| Nitrile - Blue 5 mil | 100 | 133 | 93 |
| Nitrile - Black 7 mil | 15 | 20 | 1,250 |
| Nitrile - Black 7 mil | 40 | 53 | 468 |
| Nitrile - Black 7 mil | 100 | 133 | 187 |
| Nitrile - Black 9 mil | 15 | 20 | 1,562 |
| Nitrile - Black 9 mil | 40 | 53 | 585 |
| Nitrile - Black 9 mil | 100 | 133 | 234 |
| Nitrile - Black 7 mil High Carbon | 15 | 20 | 2,500 |
| Nitrile - Black 7 mil High Carbon | 40 | 53 | 937 |
| Nitrile - Black 7 mil High Carbon | 100 | 133 | 375 |
| Nitrile - Black 9 mil High Carbon | 15 | 20 | 3,750 |
| Nitrile - Black 9 mil High Carbon | 40 | 53 | 1,406 |
| Nitrile - Black 9 mil High Carbon | 100 | 133 | 562 |

TABLE 3

Maximum Allowable Number of Treatments for Various Glove Types Using Xenon Flash Lamp.

| Glove Type | UV-C Dose (mJ/cm^2) | UV-B Dose (mJ/cm^2) | Max Treatments |
|---|---|---|---|
| None | 15 | 9 | 0 |
| None | 40 | 24 | 0 |
| Vinyl | 15 | 9 | 2 |
| Vinyl | 40 | 24 | 0 |
| Latex | 15 | 9 | 2,222 |
| Latex | 40 | 24 | 833 |
| Nitrile - Blue 5 mil | 15 | 9 | 1,388 |
| Nitrile - Blue 5 mil | 40 | 24 | 520 |
| Nitrile - Blue 5 mil | 100 | 60 | 208 |
| Nitrile - Black 7 mil | 15 | 9 | 2,777 |
| Nitrile - Black 7 mil | 40 | 24 | 1,041 |
| Nitrile - Black 7 mil | 100 | 60 | 416 |
| Nitrile - Black 9 mil | 15 | 9 | 3,472 |
| Nitrile - Black 9 mil | 40 | 24 | 1,302 |
| Nitrile - Black 9 mil | 100 | 60 | 520 |
| Nitrile - Black 7 mil High Carbon | 15 | 9 | 5,555 |
| Nitrile - Black 7 mil High Carbon | 40 | 24 | 2,083 |
| Nitrile - Black 7 mil High Carbon | 100 | 60 | 833 |
| Nitrile - Black 9 mil High Carbon | 15 | 9 | 8,333 |
| Nitrile - Black 9 mil High Carbon | 40 | 24 | 3,125 |
| Nitrile - Black 9 mil High Carbon | 100 | 60 | 1,250 |

There are various adjustments possible on the sterilization machine. Other adjustments that can be specified or implied by the markings on the gloves or other measurements may include, without limitation, the minimum amount of time between treatments, the amount of position certainty required, and/or light leakage via external or internal UV light sensors.

Optical markings may be placed anywhere on the glove that an optical sensor can reliably detect and read. In some use cases, having a consistent, known placement for a mark is sufficient for the glove position to accurately be determined. Some examples of mark placement include but are not limited to the cuffs of the glove, the top back of the hand, or the palm of the hand. These different placements each have their own benefits and require different placements of the optical sensors to detect them. Placing the marking on the cuff ensures that the hand is covered to the baffle. Placing the mark on the palm of the glove can be used to check that the hand is open before treatment. A combination of different markings in different places on the glove may in some cases provide optimal results.

Additionally, the hand coverings in embodiments shown in FIGS. 15-17 may be made of a material that is opaque to the germicidal light source used. In some use cases, this may be important because repeated, high intensity skin exposure to the germicidal light can be dangerous. For safety, the controller may in some cases only allow a certified safe hand covering to be used. External or remote digital control may be used in many sterilizing machine embodiments. For example, the sterilizing machine may connect to a web-based server to only allow customers who purchase certified hand coverings, or coverings that meet some specified or calculated criteria, to use the device, and/or limiting the amount of time or times a hand covering may be used.

Additionally, the hand coverings themselves may serve as an indication to customers of the time since the coverings were last sterilized by using color changing, time sensitive materials or pigmentation in the coverings that either changes color based on the time since the user last sterilized their hand coverings or begins changing color as soon as the hand coverings have been removed from packaging. Some exemplary embodiments include embodiments where photochromic pigmentation in the hand coverings begins at, or is brought to, a color that indicates safety by exposure to the germicidal light source in the machine and changes (or reverts) to a color that indicates that the gloves have not been sterilized in an acceptable time period when unexposed to the germicidal light source for a period of time. Additionally, photochromic pigments may be used to indicate when a glove has passed its usable life and is no longer safe to be treated. Many chemical compositions exist for photochromic pigments. There are different classes of photochromic materials or chemicals that are used in photochromic pigments that may include many different chemical formulas. Some examples of photochromic chemical classes that may be used include: Spiropyrans, spirooxazines, and diarylethenes. These photochromic material classes all react to ultraviolet light and revert to an original state when exposed to the normal conditions that a glove may experience such as being exposed to visible light or heat from the body.

Other parts may serve to indicate the state of hand coverings. For example, an indicator device can also be used to communicate with, or receive input from, a sterilizing machine to indicate when hand coverings should or must be changed and/or sterilized. In some cases, the indicator device may be carried on a user at all times. There are various different placements for an indicator device, including but not limited to: attached to a hand covering; attached to the wrist portion of a hand covering; worn on a user's wrist; attached on a shirt pocket or shirt collar; worn alongside a name tag; or worn on a belt. The same indicator device may be used for all different mounting options, or a different type of indicator device may be used.

Figure 18:
FIG. 18 depicts a fourth embodiment of a specialized hand covering with a wrist mounted indicator device.

One such embodiment is a wrist mounted indicator device shown in FIG. 18 that may indicate to customers and/or the user when the hand coverings were last treated or when treatment is, or may soon be, needed. The embodiment shown in FIG. 18 depicts a wrist mounted indicator 60 on the wrist portion of a hand covering, which incorporates a visual indication, or a light, that can turn green just after being treated, yellow when the time interval is about to expire, and red when the interval has expired. Additionally, the indicator may comprise a buzzer that emits sound or vibration when time expires and sanitization is complete. For tactile indication (including via haptic feedback), the indicator may vibrate when the time has expired or is close to expiring. This indicator may be used in combination with various other state indicators on a sterilizing machine, hand covers, and/or other indicators. The indicators may also be connected among each to synchronize their signals.

Figure 20:
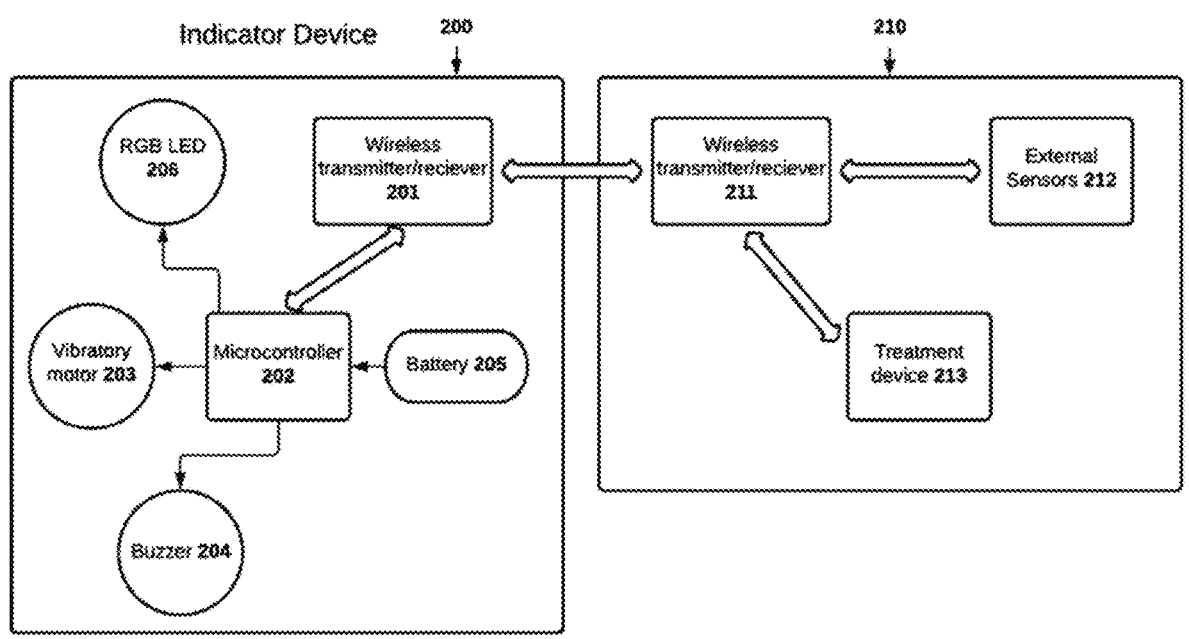
FIG. 20 depicts an embodiment of an indicator device.

An embodiment of an indicator is depicted in FIG. 20. In FIG. 20, the indicator device 200 comprises a wireless transmitter/receiver 201, a microcontroller 202, various sensory indicators such as a vibratory motor 203, LED lights 206, and a buzzer 204, a mount (not shown), and a power supply (in this case a battery 205). Various different wireless communications interfaces may be used, each with their own advantages and disadvantages. Multiple wireless communications interfaces may also be combined to maximize the use cases of the device. Wireless interfaces may include but are not limited to radio frequency, infrared, and/or ultrasonic transmitters and/or receivers. Some interfaces may allow for more information to be transferred between the compliance device and a sterilizing machine or other sensors which may be added for certain applications, allowing additional functionalities.

Sensory indicators used in the indicator device may include lights, screens, sound makers such as a buzzer or speaker, and/or a vibratory motor. More than one sensory indicator may be used in the device. For example, green, yellow, and red lights may be used to indicate the amount of time left before the hand coverings should or must be treated. After different amounts of time after treatment, the lights may change colors to indicate to the user and to others how much time is left until the hand coverings must be treated again. A screen may also be used to indicate the amount of time left before the hand coverings need to be sanitized again. Additionally, a vibration motor can also provide indication to the user to alert them when certain time intervals are reached. An auditory signal may also be used when the time interval is near and/or has been surpassed. Any combination of these indicators may be used, depending on the applicable use case(s). Sensor devices, either external or integrated into the sterilization machine, may also be used to shorten the time intervals on the indicator device.

Mounts, hook and loop fasteners (e.g., Velcro®), or straps may be used to secure the device to different places on the body. A potential power supply for the device includes but is not limited to a rechargeable battery, a disposable battery, or a wireless power source. FIG. 20 also depicts an example of how these components may interface. The indicator device 200 communicates to and/or received communications from the sanitation system 210 through a wireless transmitter/receiver (or transceiver) 201. The sanitation system 210 has a corresponding wireless transmitter/receiver 211. External sensors 212 communicate information directly or indirectly to/from the wireless transmitter/receiver 211. The treatment device 213 may also communicate to/from the wireless transmitter/receiver 211. The wireless transmitter/receiver 211 forwards the information on to the indicator device 200.

An interval circuit and/or software may be included in the indicator device to alert the service person, customer, supervisor, and/or other people in the area that a re-treatment of the hand coverings should be performed this interval may include but is not limited to a timer, point of sale input, proximity sensor, "next customer" sensor, pressure sensing pad, and/or a body heat sensor. These sensing methods help indicate when a service person has finished interacting with a customer, and thus when the hand coverings may need to be treated. An interval sensor may also be set to indicate a time period or maximum number of cycles beyond which the gloves must be replaced. For example, after N number of customers, or after each break, or after each shift, after so many units of time, and/or after some specified criteria or set of criteria.

Figure 21:
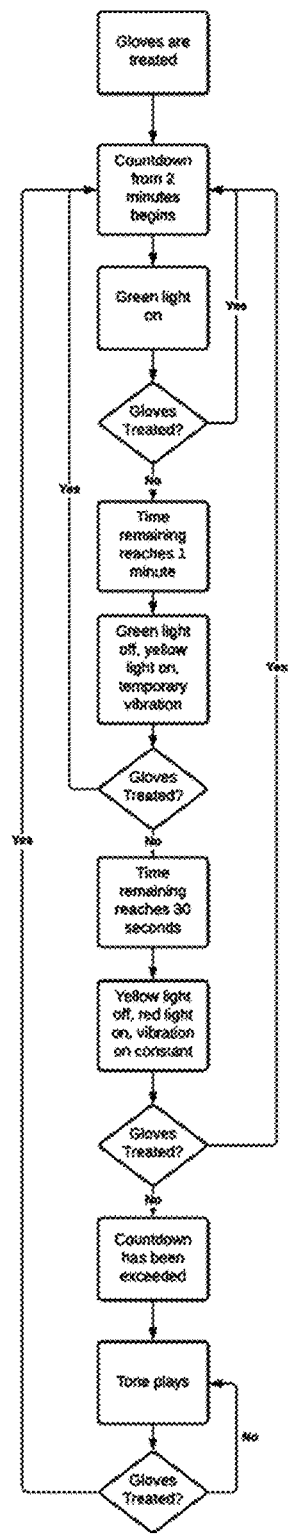
FIG. 21 depicts an embodiment of logic used by an indicator device.

FIG. 21 depicts an embodiment for an interval circuit or process that may be used with an indicator device 200 and/or the controller for the sanitization system, where the optimum time between sanitization of the hand coverings is 2 minutes. The controller may run the process and communicate instructions to the indicator device. Or the indicator device 200 may perform the process itself. The green indicator light may remain on until there is 1 minute remaining in the sanitization process. Then when 30 seconds remain, a red light may come on. If the hand coverings have not been sanitized after the 2-minute time interval, the red light may remain on, and a speaker may begin playing a tone until the gloves are treated again. Additionally, when the yellow light comes on, the device may temporarily activate a vibration motor to provide the user with tactile input as a prompt and/or to inform the time remaining before the sanitization process must occur again. When the light comes on, the vibration motor may remain active (e.g., continuously on, or pulsing at some predetermined or calculated interval(s)) until the hand coverings are treated.

Figure 22:
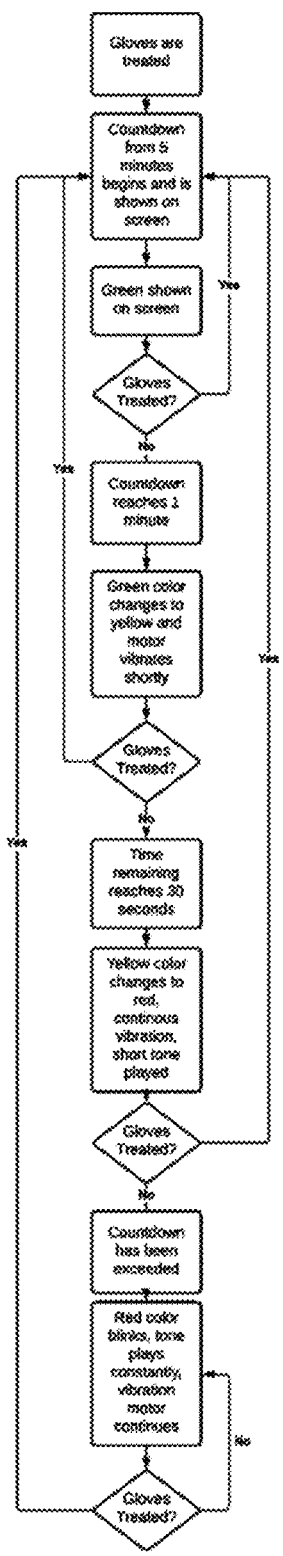
FIG. 22 depicts a second embodiment of logic used by an indicator device.

Another embodiment for an interval circuit or process for an indicator device is depicted in FIG. 22. In FIG. 22, the optimum time between treatments of hand coverings is 5 minutes. A color screen, buzzer, and vibratory motor are used in this embodiment. The screen shows the time counting down from the optimum time between sanitization treatments, which in this case is 5 minutes. The screen may show the countdown timer and an indicating color. A green color may be shown on the screen when more than 1 minute remains. A yellow color can be shown when less than 1 minute remains and more than 30 seconds remain, and/or the vibratory motor may be activated and/or pulsed. A red color can be shown when less than 30 seconds remain, and/or the vibratory motor may be activated and/or pulsed until the hand coverings are treated. If the time remaining reaches zero, the screen may flash red, and the buzzer may begin to sound. All conditions may be reset when the hand coverings are treated, and the countdown would begin again. Any combination and timing of the indicator device methods may be used.

In addition to, or as an alternative to, the indicator device, other devices such as a sterilization machine or a sensor may be used to process different events that trigger the indicator device. The design and implementation of such devices depends on the environment in which they would be used. These devices may provide inputs to the indicator device that may allow for triggering based on something other than just a time condition. These additional inputs may be relayed to the indicator device from a sterilization machine and/or the additional sensors may directly communicate to the indicator device. The additional sensor inputs may include but are not limited to a point-of-sale input, proximity sensor, "next customer" sensor, pressure sensing pad, body heat sensor, key card connected sensor, and/or an embedded equipment runtime sensor. Any event that may be detected may be related to an event that indicates interaction with a customer or potentially contaminated object. As such, many different sensors may be combined in one environment to account for different pre-programmed events that would risk the contamination of the gloves. An exemplary interaction between the indicator device and sensors is shown in FIG. 20.

Figure 23:
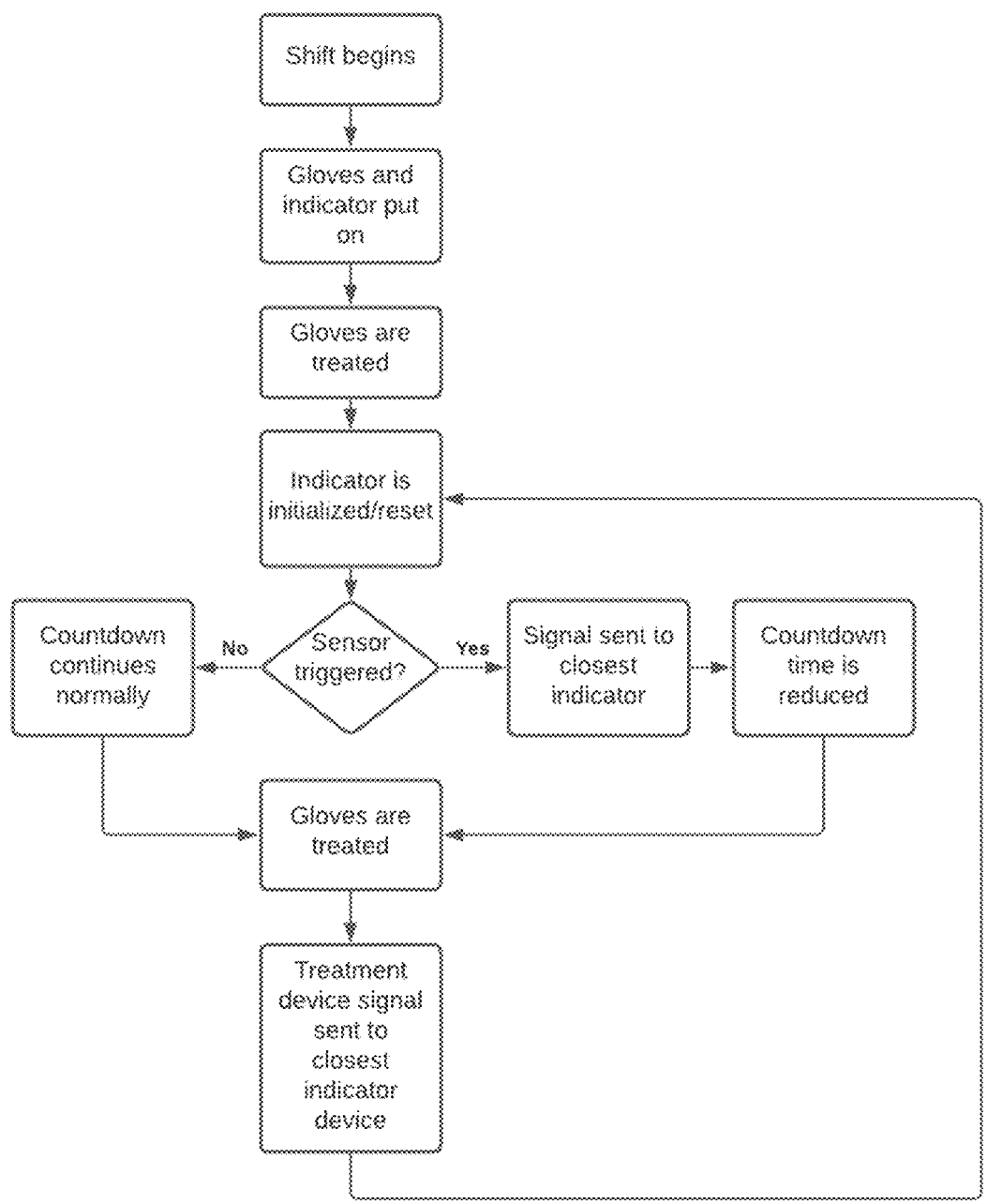
FIG. 23 depicts a second embodiment of an indicator device.

FIG. 23 depicts a process where the indicator device uses a radio frequency (RF) receiver that is embedded in the indicator to receive input from a sterilization machine. The sterilization machine has a radio frequency transmitter. (Or one or the other or both use RF transceivers.) Hand coverings or gloves with a nonspecific mark are used. At the beginning of a shift, a worker puts on their marked gloves and the indicator device. The indicator device is triggered by an internal timer with a predetermined time that, in this case, is intended to maximize compliance of glove treatment, while minimizing inconvenience. A signal is sent from the sterilization machine when a treatment is completed. This signal causes the timer in the indicator device to reset, as well as its sensory indicators. Since many sterilization machines, indicators, and gloves may be used in the same building, the indicator that has its interval reset may also be determined by its proximity to the sterilization machine. For example, the time interval on the indicator device before triggering different levels of indication may be shortened if a server at a restaurant walks from a table where they are serving to an ordering terminal or the kitchen, so that they would be reminded to treat their gloves before touching and potentially contaminating other objects or people. Using this method, a generic manufacturer marking rather than a specific marking may be used. Other triggering sensors may be used by using the same proximity-based communication.

The embodiment of FIG. 23 is also applicable to the use of an infrared light transmitter and an infrared light receiver (or one or both are IR transceivers). The infrared light transmitter may be situated in such a way that it may only communicate with the sterilization machine and other sensors it is in close proximity to, avoiding the need to address a specific indicator that is being used by a specific worker. At the beginning of a shift the indicator and gloves are put on. The gloved hands are then treated at the beginning of the shift. The indicator device begins its countdown and indicates its current status in a manner discussed above. Other sensors may interface with the indicator when they are sufficiently close to add or subtract time from the countdown.

Figure 24:
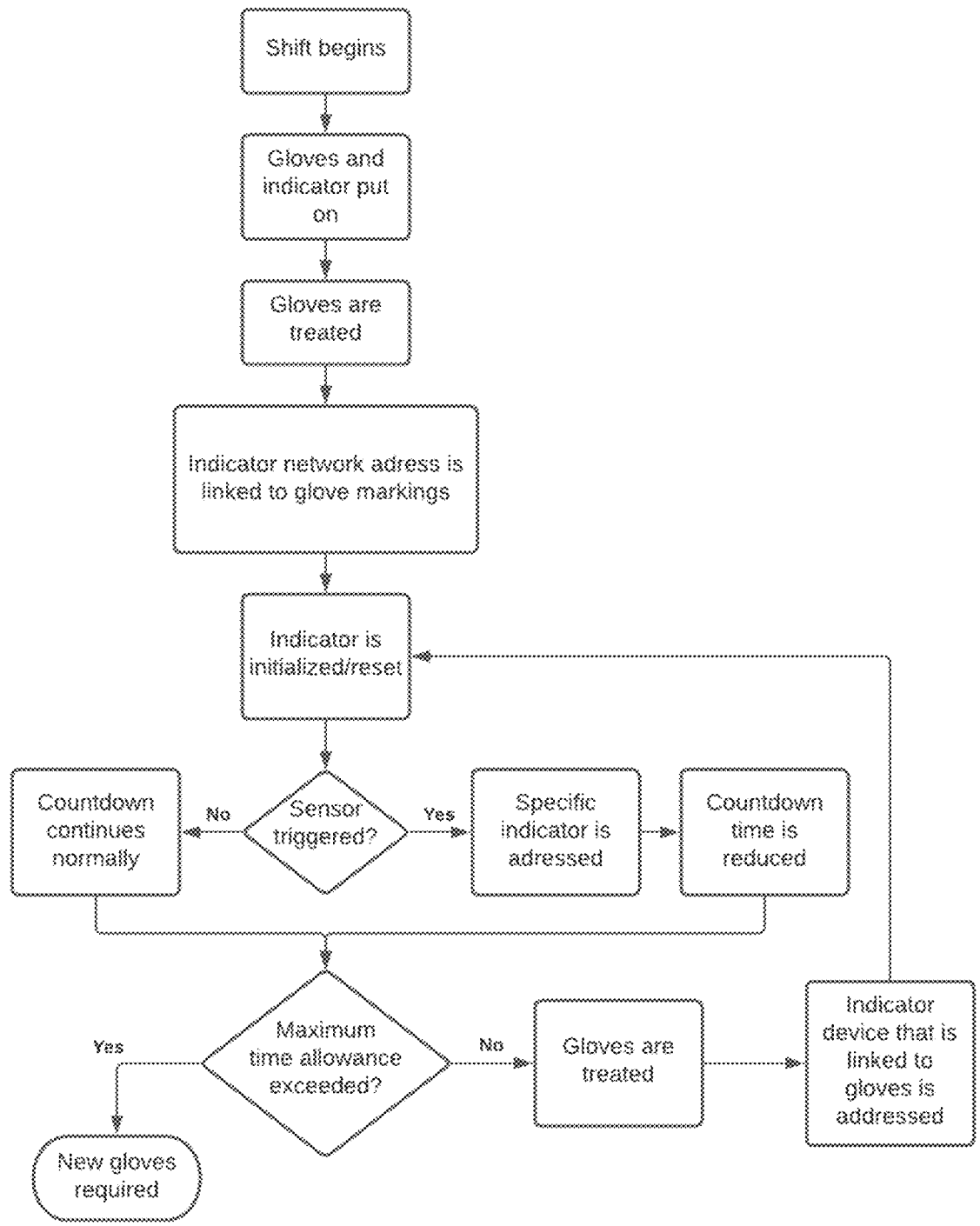
FIG. 24 depicts a third embodiment of an indicator device.

Another embodiment is shown in FIG. 24, where a radio frequency network is used. In this radio frequency network, each device is addressable. This may include using commercially defined RF standards such as various Bluetooth and/or Wi-Fi versions and gloves with unique markings on each glove. Proximity sensor beacons are also installed in the building because for this specific use case, moving from certain areas of the building to another is likely to cause contamination of the surface of the gloves that should be treated before interacting with others or objects. At the beginning of a shift a worker would put on the gloves with the unique markings. They would also put on the indicator device. A button or other sensor on the device would be pushed or in some way activated near the sterilization machine and the gloved hands would be treated and the network of sterilization machines, indicators, and/or other sensors would establish an association with the markings on the glove(s) and that specific indicator for the duration of the shift. With this association, when a sterilization machine treats a pair of gloves, the indicator paired with that pair of gloves may be addressed on the network and communicated with to be reset. Additionally, other sensors in the network may communicate with a specific indicator, to which its measurements or sensed inputs apply, in order to modify the indicator's time interval based on what impact the detected action or event would have on the cleanliness of the gloves.

Optical sensors may determine the position of the gloves in relation to the opening of the baffles on the sterilization machine including hand depth and angle. To determine the age of gloves in an implementation where all gloves from a verified manufacturer have the same mark, data about how often an establishment is purchasing new gloves and when those gloves were manufactured. To determine the number of times a glove has been treated in this implementation, shift change data may be used, a basic count on the sterilization machine may be used if a server remains at the same sterilization machine for a shift, an average of the number of treatments for each server may be used by aggregating data from all the sterilization machines in an establishment, or the indicator device may be used to track the number of times it has been reset and wirelessly communicate with the sterilization machine to ensure the gloves have not been treated too many times to be safe.

Once an employee wearing the hand coverings finishes dealings with a customer, the employee will insert their hands into the machine. The machine will sense the position of the gloved hands. When the hands have been inserted at the proper depth, the sensor will detect when the hands have reached the optimal position triggering the controller. Only when the hands are detected at a proper or an acceptable depth, will the controller activate the germicidal light source.

Pathogens can develop resistance to ultraviolet light. There are two main mechanisms of ultraviolet resistance in pathogens: photo-protection and DNA repair. Photo-protection is of the highest concern when addressing the issue of ultraviolet resistance, since it can increase the required ultraviolet dose to kill or inactivate pathogens much more than DNA repair mechanisms, since the damage that DNA repair mechanisms can solve is limited. Some photo-protection methods work by increasing the absorption of ultraviolet light in the exterior of the pathogen, which protects the genetic material of the pathogen. Other forms of photoprotection do exist but absorption is the particular mechanism that is being addressed. There is no generally accepted solution to address Ultraviolet resistance in pathogens. A mix of different disinfecting methods are often combined to attempt to minimize the impact of resistance to any particular disinfecting method. This has caused even more dangerous pathogens that are resistant to a multitude of different disinfecting methods and leads to different items being disinfected less often.

Ultraviolet resistance is also of special import when considering its widespread use in scenarios where the velocity of pathogens is high, such as when there are many interactions between people such as at places of travel or other high-density areas. The high velocity of pathogens makes resistance to different disinfecting methods develop more quickly, and such resistant strains of pathogens may quickly become the dominant strain, making commonly used methods of disinfection less effective.

The increased absorption of UV provided by a photo-protection mechanism makes it significantly more difficult to kill or deactivate pathogens, although it allows for another weakness that can be targeted using similar ultraviolet light sources, in a different configuration. By using high energy pulses of light energy, the absorptive characteristics of the photo-protective coating can be exploited to create higher surface temperatures that ultimately lead to a greater thermal shock in the exterior of the pathogen. Therefore, a source of UV light, when modulated in a different manner, can be used to kill or deactivate pathogens that would typically require extraordinarily high doses of UV light, which necessitates longer exposure or higher intensity of light. In many cases, implementing either of these measures (longer exposure or higher light intensity) is not feasible.

Ultraviolet resistant pathogens may require doses over ten times as high as their non-UV resistant counterparts and many systems are designed with a specific target UV dose that would be much too low for UV resistant pathogen and cannot be increased because of the existing design constraints. Additionally, with even higher doses, a similar problem may occur where even more UV resistant pathogens emerge that again cannot be disinfected with existing equipment.

Instead, a balance can be struck where pathogens that are UV resistant can be kept in check and killed or deactivated by a single apparatus without changing the ultraviolet dose. When pathogens develop ultraviolet resistance, they are necessarily making a tradeoff of absorbing more light energy in their exterior whether it be the protein shell in viruses or spores, or the cell wall of a bacterium. With traditional ultraviolet light sources, such a tradeoff allows for their genetic material to be protected from the ultraviolet light, while posing little disadvantage to the pathogen in such an environment. When using a high energy pulse of UV light, the higher absorption of UV light in the photo-protective material of the pathogen makes it absorb more thermal energy from the UV light, and therefore can cause a greater thermal shock in the pathogen. Thermal shock has been shown to be an effective method of killing or deactivating pathogens, but it has not been used in such a way to address the UV resistance of pathogens. Such a relationship is very beneficial for all aspects of UV disinfection since it allows for a lower ultraviolet dose to be used to kill or deactivate even highly ultraviolet resistant pathogens. Additionally, pulsing of the ultraviolet light decreases the incidence of ultraviolet resistance since ultraviolet resistant pathogens would not be preferentially selected since the thermal shock triggered through the pulsing would target their photo-protective elements, while the general nature of the ultraviolet light would target the non-ultraviolet-resistant pathogens.

Some pathogens, such as spores, are not only resistant to ultraviolet light, but also heat and many other disinfecting methods. Pulsed ultraviolet light (i.e., 250 ms or less of UV radiation at some certain power output) is useful against these kinds of very resilient pathogens. These pathogens still may be susceptible to thermal shock, although repeated thermal cycles may be necessary to deactivate or kill these pathogens. The most effective time between pulses can be determined to provide the greatest effect in the shortest period of time for specific known pathogens. Repeated thermal cycles will create high stress in pathogens which can provide a greater germicidal effect.

The light source will remain on or will be pulsed for an adequate amount of time to eliminate, deactivate, or disable all or a significant amount of surface pathogens on the hand coverings. Table 4 and Table 5 show the amount of time required using a UV-C light source to achieve a target UV-C dose to obtain a 3 log reduction for a generic pathogen. In Table 5, the charge time represents a hypothetical time necessary to charge the UV-C light source capacitor to enable pulsing of the light.

TABLE 4

Power output, dose, and amount of time required to kill or inactivate a generic pathogen.

| UV-C Power Output (W) | Target UV-C Dose In (mJ/cm^2) | Time Required (s) |
|---|---|---|
| 1 | 6 | 45 |
| 10 | 6 | 4.5 |
| 50 | 6 | 0.9 |
| 50 | 10 | 1.5 |
| 100 | 6 | 0.45 |
| 100 | 10 | 0.75 |
| 100 | 15 | 1.125 |
| 200 | 15 | 0.5625 |
| 200 | 40 | 1.5 |
| 500 | 200 | 3 |
| 1000 | 200 | 1.5 |

TABLE 5

Time required to achieve a target UV-C dose given UV-C energy
per pulse, pulse duration, and rest time (time between pulses).

| UV-C Energy per pulse (J) | Target Dose (mJ/cm^2) | Number of Pulses | Pulse Duration (ms) | Rest Time (ms) | Total Time (s) |
|---|---|---|---|---|---|
| 0.05 | 10 | 2667 | 0.05 | 0.1 | 0.40 |
| 0.05 | 15 | 4000 | 0.05 | 0.1 | 0.60 |
| 0.05 | 40 | 10,667 | 0.05 | 0.1 | 1.60 |
| 0.05 | 150 | 40,000 | 0.05 | 0.1 | 6.00 |
| 0.5 | 10 | 267 | 0.5 | 0.5 | 0.27 |
| 0.5 | 15 | 400 | 0.5 | 0.5 | 0.40 |
| 1 | 40 | 533 | 1 | 1 | 1.07 |
| 2 | 150 | 1,000 | 1 | 1 | 2.00 |
| 4 | 300 | 1,000 | 1.5 | 1.5 | 3.00 |
| 6 | 900 | 2,000 | 1.5 | 1.5 | 6.00 |
| 200 | 10 | 1 | 50 | N/A | 0.05 |
| 200 | 15 | 1 | 50 | N/A | 0.05 |
| 200 | 40 | 3 | 50 | 500 | 1.00 |
| 500 | 15 | 1 | 60 | N/A | 0.06 |
| 500 | 40 | 1 | 60 | N/A | 0.06 |
| 2,000 | 150 | 1 | 100 | N/A | 0.10 |
| 2,000 | 300 | 2 | 100 | 1,250 | 1.35 |
| 4,000 | 900 | 3 | 100 | 1,250 | 2.60 |

Log reduction is a mathematical term that is used to express the relative number of living microbes that are eliminated by disinfection. The term "disinfection" can sometimes be used in different fields to mean a specific log reduction of a specific pathogen. In the following examples, the term "disinfection" is used as a way to describe a range of log reductions for various pathogens.

For example, the 6 mJ/cm^2, target UV-C dose is sufficient to provide a higher than single log reduction of SARS-CoV-2 virus, at least 2 log reduction for *Staphylococcus aureus*, almost a single log reduction for *Streptococcus faecalis*, and a 3 log reduction in *Salmonella typhimurium* (ATCC 6539), and many more pathogens. [Malayeri, Adel Haji et al. "Fluence (UV Dose) Required to Achieve Incremental Log Inactivation of Bacteria, Protozoa, Viruses and Algae." IUVA News vol. 18:3. Fall 2016, https://uvsolutionsmag.com/stories/pdf/archives/180301_UVSensitivityReview_full.pdf] [Heßling, Martin et al. "Ultraviolet irradiation doses for coronavirus inactivation—review and analysis of coronavirus photoinactivation studies." GMS hygiene and infection control vol. 15 Doc08. 14 May 2020, doi:10.3205/dgkh000343].

The 10 mJ/cm^2 target dose can achieve higher levels of reduction in pathogens listed in the 6 mJ/cm^2 target dose in addition to a single log reduction of Murine norovirus, at least single log reduction of various types of Poliovirus, at least single log reduction of various Coxsackievirus strains, over 5 log reduction of *Helicobacter pylori*, and more.

Higher target doses provide higher log reductions for all pathogens listed. 40 mJ/cm^2 is a UV-C dose that can cause significant decreases in most pathogens and is often used in water treatment for its high effectiveness against an array of pathogens. [Templeton, Michael. "Basic Principles of UV Disinfection." Department of Civil and Environmental Engineering, Imperial College London. https://www.un-ihe.org/sites/default/files/3_-_templeton.pdf]. Other, higher energy levels are effective against more UV-C resistant pathogens such as spores and UV-C resistant virus strains and may be useful in settings where high cleanliness is necessary such as in the medical industry.

While some lower UV-C doses are less effective, the doses may add cumulatively for multiple treatments. For example, if a customer is interacting with a server and a pathogen that requires a dose of 60 mJ/cm^2 is transferred to the surface of the gloves for a given reduction, after one treatment of the surface of the gloves at 6 mJ/cm^2 the pathogen is still significantly reduced and after each successive treatment, more reduction in the pathogen occurs, and the 60 mJ/cm^2 dose is reached after 10 treatments. The relationship between the reduction in pathogens between treatments may not scale linearly, but the effect may allow for lower UV-C doses to still significantly decrease transmission.

The calculations are approximations of the time required to achieve a UV-C dose with a constant output light source of known power. Constant output sources may include low pressure mercury lamps, medium pressure mercury lamps, UV-C LED arrays, UV-C lasers, and more that are driven with a constant output. For these calculations, the surface area of two average sized hands is about 1 square meter. The coefficient of reflection is assumed to be 0.75, which can approximate an aluminum reflective enclosure. Since, the fingertips are the most important touched surface, it is assumed that they are the area that is being considered, although the coefficient of reflection of 0.75 is conservative and may work to approximate other areas on the surface of the gloves. The time required is calculated by multiplying the target dose by the reflection coefficient and dividing by the surface area of two average hands multiplied by the UV-C power output.

After the light source has been emitting for an adequate duration to sanitize the hand coverings, the machine may provide an indication whether visual, auditory, tactile, and/or through other signals such an electronic signal to another device indicating the exposure of the gloved hands has concluded.

Additionally, other indicating devices such as indicating bracelet, photochromic gloves, and interval circuit and/or hardware may indicate to the server and customers when the hand coverings have been treated and the server is ready for the next interaction. The user will be prompted by a signal to remove their hands and safely interact with the next customer.

In some circumstances, treating the surface of the gloves alone may not maintain cleanliness. When the surface of the gloves comes into contact with a significant amount of potentially contaminated liquid or solid matter, the ability for the surface to be treated is greatly decreased. Additionally, even if all of the potential biological contaminants mixed with a significant amount of liquid or solid matter could be killed or inactivated from the surface of the gloves, a great degree of physical contamination would still occur without changing gloves. It is important to acknowledge the importance of situations where gloves must be changed rather than treated and a method to ensure that gloves are always changed in those situations.

It is possible that changing gloves, like many other biosecurity measures such as hand washing after potential physical contamination, can often be forgotten or even consciously neglected. Changing gloves in medical environments, food processing, and more is essential in preventing unnecessary infections and pathogen transmission. The indicator device described can also be used to alert and enforce when gloves must be changed. This can be done in a system with the gloves, the sterilizing machine, and external sensors or in a system that omits the sterilizing machine.

To determine when gloves must be changed sensors similar to the ones described to trigger the indicator to prompt a user to treat their gloves may be used to trigger the indicator to prompt a user to change their gloves. Proximity sensors, equipment sensors, and more may be used to determine times when glove changes may be necessary or beneficial. With these sensors and potentially more, the device can determine situations where there is a high chance that the gloves have been physically contaminated and need to be changed after an interaction. For example, at a doctor's office if a doctor or nurse enters a room where blood is typically drawn, the indicator device can alert that a glove change is necessary after leaving the room.

Another example is that in most any environment, if an employee uses the restroom, they must change their gloves. Equipment such as meat freezers or medical devices that are associated with physical contamination of the surface of the gloves can also cause an indication that a glove change is necessary. Another use case is designating objects that certain workers should not touch, or they will be required to change their gloves. Some examples of such situations are if a waiter at a restaurant touches bussing equipment, if a non-janitorial employee touches janitorial supplies such as a mop, if a secretary at a hospital touches items that are known to be contaminated with bodily fluids, and many more. This may be achieved by proximity sensing. A similar indicating scheme to the ones described to prompt gloves to be treated can be used to prompt a user to change their gloves.

To ensure that the gloves are changed whenever an event that requires a glove change is detected by the indicator device, the markings on the gloves can either be scanned by the indicator device itself, a sterilizing machine, or an external scanning device to prove that the gloves have been changed. Specific or nonspecific marked gloves may be used. With a specific mark, a glove change can be electronically verified since each glove has a different mark that can be detected. With a nonspecific mark, other factors such as the indicator device physically attaching to the cuff of the glove may serve as a verification that gloves have been changed.

What is claimed is:

1. A method of sanitizing a hand covering comprising:
   providing a sterilizing machine for use in a ultraviolet (UV) sterilization process, the sterilizing machine comprising an enclosure and a UV light source;
   obtaining information from a mark on a hand covering on a user;
   basing the power output of the UV light source at least in part on information obtained from the mark on the hand covering;
   initiating the UV sterilization process wherein the UV light source is powered on prior to the user inserting the hand covering into the sterilizing machine; and
   inserting the hand covering on the user into the sterilizing machine.

2. The method of claim 1 further comprising:
   placing the UV light source into a lower power mode after the UV sterilization process is complete.

3. The method of claim 1 further comprising:
   outputting, to the user of the hand covering, a signal using an indicator device worn by the user, that the UV sterilization process is complete, wherein the indicator device comprises a sensory indicator, a wireless transceiver, a microcontroller, and a power supply.

4. The method of claim 3 wherein the sterilizing machine has a drive assembly with bearings mounted to the enclosure, and brushes mounted to the bearings.

5. The method of claim 3 further comprising:
   indicating to the user, by the indicator device, that the hand covering will, after a further predetermined period of time, need to be changed.

6. The method of claim 3, wherein the indicator device is attachable to a user's shirt.

7. The method of claim 1 further comprising:
   outputting, to an indicator device worn by the user, a signal that the UV sterilization process is complete, wherein the indicator device comprises a sensory indicator, a wireless transceiver, a microcontroller, and a power supply.

8. The method of claim 7 wherein the sterilizing machine has a drive assembly with bearings mounted to the enclosure, and brushes mounted to the bearings.

9. The method of claim 7 further comprising:
   indicating to the user, by the indicator device, that the hand covering will, after a further predetermined period of time, need to be sterilized.

10. The method of claim 7, wherein the indicator device is attachable to a user's shirt pocket.

11. The method of claim 1 further comprising:
    receiving, by an indicator device worn by the user, a signal that a second UV sterilization process for the hand covering should begin, wherein the indicator device comprises a sensory indicator, a wireless transceiver, a microcontroller, and a power supply.

* * * * *